US011447830B2

(12) United States Patent
Lin et al.

(10) Patent No.: US 11,447,830 B2
(45) Date of Patent: Sep. 20, 2022

(54) GENE SIGNATURES TO PREDICT DRUG RESPONSE IN CANCER

(71) Applicant: Board of Regents, The University of Texas System, Austin, TX (US)

(72) Inventors: Shiaw-Yih Lin, Bellaire, TX (US); Daniel McGrail, Houston, TX (US); Gordon Mills, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/490,588

(22) PCT Filed: Mar. 5, 2018

(86) PCT No.: PCT/US2018/020932
§ 371 (c)(1),
(2) Date: Sep. 2, 2019

(87) PCT Pub. No.: WO2018/161081
PCT Pub. Date: Sep. 7, 2018

(65) Prior Publication Data
US 2020/0017918 A1 Jan. 16, 2020

Related U.S. Application Data

(60) Provisional application No. 62/466,829, filed on Mar. 3, 2017.

(51) Int. Cl.
C12Q 1/68 (2018.01)
C12Q 1/6886 (2018.01)
G16H 50/30 (2018.01)
G16B 40/10 (2019.01)

(52) U.S. Cl.
CPC ........... *C12Q 1/6886* (2013.01); *G16B 40/10* (2019.02); *G16H 50/30* (2018.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 2009/0030016 | A1 | 1/2009 | Gandhi et al. | |
| 2014/0364434 | A1 | 12/2014 | Daeman et al. | |
| 2016/0010159 | A1* | 1/2016 | Lin | A61K 31/167 |
| | | | | 514/212.06 |

FOREIGN PATENT DOCUMENTS

| WO | WO 2011-058367 | 5/2011 | |
| WO | WO-2011058367 A2 * | 5/2011 | ........... C12Q 1/6816 |
| WO | WO 2013-153130 | 10/2013 | |
| WO | WO 2015-135035 | 9/2015 | |

OTHER PUBLICATIONS

Santarpia et al. (The Oncologist 2013;18:1063-1073) (Year: 2013).*
NetAffx Show Results. Query capn13 array HG-U133 Plus 2. Obtained from https://www.affymetrix.com/analysis.netaffx/showresults.affx on Apr. 23, 2021. 1 page. (Year: 2021).*
NetAffx Show Results. Query ZNF880 array HG-U133 Plus 2. Obtained from https://www.affymetrix.com/analysis.netaffx/showresults.affx on Apr. 23, 2021. 1 page. (Year: 2021).*
NetAffx Show Results. Query Iyar array HG-U133 Plus 2. Obtained from https://www.affymetrix.com/analysis.netaffx/showresults.affx on Apr. 23, 2021. 1 page. (Year: 2021).*
NetAffx Show Results. Query npm3 array HG-U133 Plus 2. Obtained from https://www.affymetrix.com/analysis.netaffx/showresults.affx on Apr. 23, 2021. 1 page. (Year: 2021).*
Kulkarni et al. (Current Protocols in Molecular Biology 25B.10.1-25B.10.17, Apr. 2011). (Year: 2011).*
Barretina et al., "The Cancer Cell Line Encyclopedia enables predictive modelling of anticancer drug sensitivity," *Nature*, 483:603-607, 2012.
Brown et al., "PARP inhibitors: the race is on," *Br. J. Cancer*, 114:713-715, 2016.
Bruna et al., "A biobank of breast cancer explants with preserved intra-tumor heterogeneity to screen anticancer compounds," *Cell*, 167(1):260-274, 2016.
Cardoso et al., "Clinical application of the 70-gene profile: The MINDACT trial," *J. Clin. Oncol.*, 26:729-735, 2008.
Costello et al., "A community effort to assess and improve drug sensitivity prediction algorithms," *Nat. Biotechnol.*, 32(12):1202-1212, 2014.
Cowin et al., "Profiling the cancer genome," *Annu. Rev. Genomics Hum. Genet.*, 11:133-159, 2010.
Farmer et al., "Targeting the DNA repair defect in BRCA mutant cells as a therapeutic strategy," *Nature*, 434:917-921, 2005.
Helleday, "The underlying mechanism for the PARP and BRCA synthetic lethality: Clearing up the misunderstandings," *Mol. Oncol.*, 5:387-393, 2011.
Herr et al., "A genome-wide IR-induced RAD51 foci RNAi screen identifies CDC73 involved in chromatin remodeling for DNA repair," *Cell Discov.*, 1:15034, 2015.
Kang et al., "A DNA repair pathway-focused score for prediction of outcomes in ovarian cancer treated with platinum-based chemotherapy," *J. Natl. Cancer Inst.*, 104:670-681, 2012.
Kao et al., "Molecular profiling of breast cancer cell lines defines relevant tumor models and provides a resource for cancer gene discovery," *PLoS One*, 4:e6146, 2009.
Kelly et al., "A phase I/II study of sepantronium bromide (YM155, survivin suppressor) with paclitaxel and carboplatin in patients with advanced non-Small-Cell lung cancer," *Ann. Oncol.*, 24:2601-2606, 2013.

(Continued)

*Primary Examiner* — Juliet C Switzer
(74) *Attorney, Agent, or Firm* — Parker Highlander PLLC

(57) ABSTRACT

Methods for identifying and treating cancers that are DNA repair, such as homologous recombination (HR) repair, defective or sensitive to PARP inhibitors or platinum-based therapy. In some aspects, DNA repair, such as HR repair, defective cancers are treated with a PARP inhibitor therapy or cisplatin. Methods for sensitizing cancers to a PARP inhibitor therapy are also provided.

30 Claims, 24 Drawing Sheets

(56) References Cited

OTHER PUBLICATIONS

Koboldt et al., "Comprehensive molecular portraits of human breast tumours," *Nature*, 490:61-70, 2012.

Konstantinopoulos et al., "Gene Expression Profile of BRCAness That Correlates With Responsiveness to Chemotherapy and With Outcome in Patients With Epithelial Ovarian," *Cancer. J. Clin. Oncol.*, 28:3555-3561, 2010.

Li et al., "Cisplatin regulates the MAPK kinase pathway to induce increased expression of DNA repair gene ERCC1 and increase melanoma chemoresistance," *Oncogene*, 31:2412-2422, 2012.

Livraghi and Garber, "PARP inhibitors in the management of breast cancer: current data and future prospects," *BMC Med.*, 13:188, 2015.

PCT International Search Report and Written Opinion Issued in international Application No. PCT/US2018/020932, dated May 25, 2018.

Pierce et al., "XRCC3 promotes homology-directed repair of DNA damage in mammalian cells," *Genes Dev.*, 13:2633-2638, 1999.

Querfeld et al., "The selective protein kinase C beta inhibitor enzastaurin induces apoptosis in cutaneous T-cell lymphoma cell lines through the AKT pathway," *Journal of Investigative Dermatology*, 126:1641-1647, 2006.

Sparano et al., "Prospective Validation of a 21-Gene Expression Assay in Breast Cancer," *N. Engl. J. Med.*, 373(21):2005-2014, 2015.

Tan and Tan, "Genetics: An 18-gene signature (ColoPrint®) for colon cancer prognosis," *Nat. Rev. Clin. Oncol.*, 8:131-133, 2011.

Wallden et al., "Development and verification of the PAM50-based Prosigna breast cancer gene signature assay," *BMC Med. Genomics*, 8:54, 2015.

Yang et al., "Genomics of Drug Sensitivity in Cancer (GDSC): A resource for therapeutic biomarker discovery in cancer cells," *Nucleic Acids Res.*, 41:D955-961, 2013.

\* cited by examiner

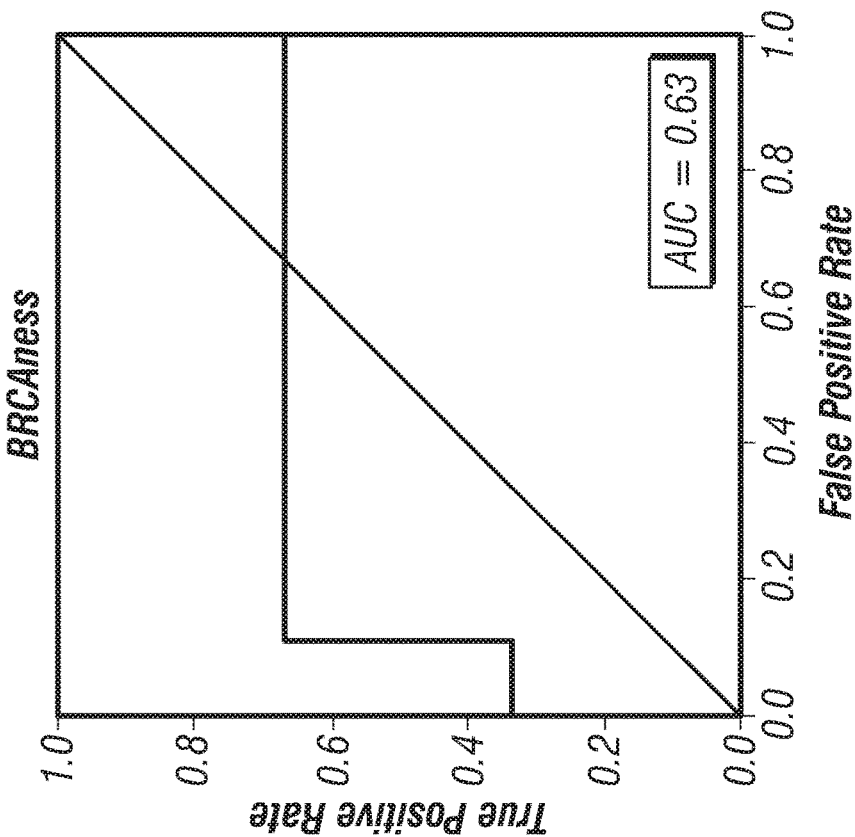
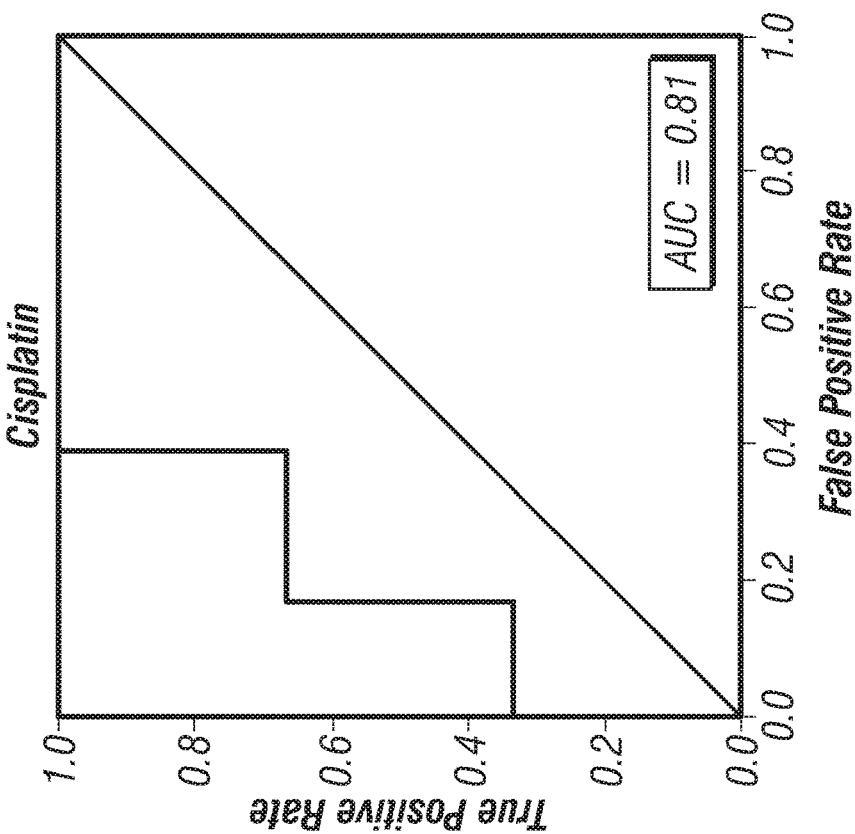
FIG. 2A
FIG. 2B

US 11,447,830 B2

GENE SIGNATURES TO PREDICT DRUG RESPONSE IN CANCER

This application is a national phase application under 35 U.S.C. § 371 of International Application No. PCT/US2018/020932, filed Mar. 5, 2018, which claims the benefit of U.S. Provisional Patent Application No. 62/466,829, filed Mar. 3, 2017, the entirety of each of which is incorporated herein by reference.

This invention was made with government support under Grant No. W81XWH-10-1-0558 awarded by the U.S. Department of the Army. The government has certain rights in the invention.

BACKGROUND OF THE INVENTION

1. Field of the Invention

The present invention relates generally to the field of molecular biology and oncology. More particularly, it concerns methods for identifying PARP inhibitor-sensitive cancers and methods of for enhancing PARP inhibitor treatment.

2. Description of Related Art

The personalized management of cancer relies on an exponential understanding of various cancer types, and of their subtypes, at both the genotypic and phenotypic levels (Bast et al., 2014). On a single molecule level, pre-clinical pharmaceutical testing in cancer cell line panels have guided early stage clinical trials, such as with the use of gefitinib for epidermal growth factor receptor mutant lung cancers, imatinib mesylate for the fusion BCR-Ab1 oncogene in leukemia (Scappini et al., 2004), and trastuzumab or lapatinib in HER2/ERBB2 amplified breast cancers (Paez et al., 2004; Konecny et al., 2006).

Unfortunately, for the majority of therapeutic molecules, a single gene assay is insufficient to accurately predict drug response. Transcriptomic analysis represents one of the most promising approaches to overcome this challenge, and relies on robust gene expression signatures designed to capture the core common features indicative of drug sensitivity, regardless of their precise molecular origin (Costello et al., 2014). Rapid technological advances are quickly making clinical implementation of these multi-gene signatures feasible (Cowin et al., 2010). For example, the 50-gene Prosigna based on the PAM50 gene set has been FDA approved (Wallden et al., 2015) and a 70-gene signature led to the development of MammaPrint, a commercially available DNA microarray that aids in the prediction of low-grade breast cancer prognosis, has recently completed phase III trials (Cardoso et al., 2016). Other signatures have shown promise to predict genomic instability in cancers (Pitroda et al., 2014). Many studies have suggested that human cancer cell lines model many "omic" aspects of tumors, thereby making them representative proxies for the identification and evaluation of effective therapeutic interventions (Garnett et al., 2012). However, it has been challenging to implement successful approaches that leverage transcriptomic data from cells lines to predict patient responses.

In contrast to the above-mentioned targeted therapies that rely on mutations/amplifications in a single gene for identification of patients likely to benefit, PARP inhibitors work more indirectly by synthetic lethality in patients with mutated BRCA1 or BRCA2 (Bryant et al., 2005). Both BRCA1 and BRCA2 are key components of the homologous recombination (HR) double-stranded break DNA repair pathway, resulting in increased risk of developing breast, ovarian, lung, bladder, and other cancers if they are mutated. It is proposed that PARP inhibition (PARPi) selectively targets BRCA-mutant cells by increasing DNA single stranded breaks that result in irreparable DNA double-strand breaks during replication, culminating in cell death. Early trials in treating BRCA-mutant ovarian cancer patients were so successful that olaparib from AstraZeneca was granted accelerated approval for BRCA-mutant ovarian cancer and rucabarib from Clovis Oncology was given breakthrough therapy designation by the FDA (Brown et al., 2016).

Despite this promise, stratification of patients for PARP inhibitor therapy by BRCA status is proving suboptimal, with the majority of BRCA-mutant patients failing to show objective responses, clearly necessitating approaches for better identification of patient populations for PARPi treatment as clinical trial objective response rates rarely exceed 50% (Livraghi and Garber, 2015). Thus, a clinical need remains for the improvement of methods to enhance PARP inhibitor efficacy.

SUMMARY OF THE INVENTION

In a first embodiment, the present disclosure provides a method of identifying a cancer as DNA repair (e.g., homologous recombination (HR) repair) defective comprising obtaining a sample of the cancer; determining the expression levels of at least 3 of the genes selected from the group consisting of those listed in Table 1 or Table 2 in the sample; and identifying the cancer as DNA repair (e.g., HR repair) defective if the expression level of said genes are up- or down-regulated compared to a control expression level; or identifying the cancer not DNA repair (e.g., HR repair) defective if said genes are not up- or down-regulated compared to a control expression level. In some aspects, DNA repair is HR repair. In some aspects, a cancer identified as DNA repair (e.g., HR repair) defective is further defined as a therapy sensitive (e.g., PARP inhibition or platinum-based therapy) cancer and a cancer identified as not DNA repair (e.g., HR repair) defective is further defined as a therapy resistant cancer. In another embodiment, there is provided a method of identifying a cancer as therapy sensitive or therapy resistant comprising obtaining a sample of the cancer; determining the expression levels of at least 3 of the genes selected from the group consisting of those listed in Table 1 or Table 2 in the sample; and identifying the cancer as therapy sensitive if the expression level of said genes are up- or down-regulated compared to a control expression level; or identifying the cancer therapy resistant if said genes are not up- or down-regulated compared to a control expression level.

In certain aspects, the therapy is PARP inhibitor and/or a platinum-based therapy. In some aspects, the platinum-based therapy is cisplatin. In certain aspects, the method may be defined as an in vitro method. The sample may comprise blood, saliva, urine, or a tissue biopsy.

In one aspect, a cancer may be identified as DNA repair (e.g., HR repair) defective or therapy sensitive if at least one gene from Table 1A or Table 2A is up-regulated relative to a control expression level. Alternatively, the cancer may not be identified as DNA repair (e.g., HR repair) defective or therapy resistant if the gene is not up-regulated relative to a control expression level. Conversely, in another aspect, a cancer may be identified as DNA repair (e.g., HR repair) defective or therapy sensitive if at least one gene from Table 1B or Table 2B is down-regulated relative to a control expression level. Alternatively, the cancer may not be identified as DNA repair (e.g., HR repair) defective or therapy resistant if the gene is not down-regulated relative to a control expression level.

In certain aspects, the method may comprise determining the expression levels of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, or 147 of the genes listed in Table 1. In certain aspects, the method may comprise determining the expression levels of at least 4, 5, 6, 7, 8, 9, 10, 11, 12, 13, 14, 15, 16, 17, 18, 19, 20, 21, 22, 23, 24, 25, or 26 of the genes listed in Table 2. In certain aspects, the method may comprise determining the expression levels of 10-50, 20-100, 50-150, or 100-147 of the genes listed in Table 1, or any range derivable therein. In another aspect, the method may comprise determining the expression levels of all 147 genes listed in Table 1 or all 26 genes listed in Table 2.

In a further aspect, a method of the embodiments may be defined as a method of determining a prognosis of a cancer. Thus, in some aspects, identifying a cancer as DNA repair (e.g., HR repair) defective is indicative of better overall survival. In another aspect, identifying a cancer as DNA repair (e.g., HR repair) defective further comprises identifying a patient having the cancer as a candidate for PARP inhibitor (PARPi) therapy. In another aspect, identifying a cancer as DNA repair (e.g., HR repair) defective further comprises identifying a patient having the cancer as a candidate for therapy with particular DNA damaging agents (e.g., platin derivatives or radiation, particularly cisplatin).

In some aspects, the method further comprises isolating RNA from the sample. In certain aspects, determining the expression levels may comprise preforming RT-PCR, a hybridization, transcriptome analysis, RNAseq, a Northern blot, a Western blot, or an ELISA. For example, determining the expression levels can comprise performing an array hybridization. In one aspect, transcriptome analysis may comprise obtaining sequence information of expressed RNA molecules. In some aspects, the method may comprise using genes of Table 1 or Table 2 with refined coefficients. In certain aspects, the refined coefficients may comprise taking a positive coefficient as +1 and a negative coefficient as −1. In other aspects, the refined coefficients may be based on results from the method of determining the expression level (i.e., the platform for determining the gene signature).

In a further embodiment, the present disclosure provides a method of treating a cancer patient comprising selecting a patient determined to have a DNA repair (e.g., HR repair) defective cancer based on the expression levels in a sample of the cancer of at least 3 genes listed in Table 1 or Table 2; and treating the selected patient with a PARP inhibitor (PARPi) or a platin analog therapy (e.g., cisplatin). In some aspects, the therapy, such as a PARP inhibitor, may be used in a maintenance setting, such as to help prevent recurrence after a subject is treated with a primary course of therapy, such as chemotherapy. In certain aspects, the method may further comprise administering a second anti-cancer therapy to the subject in conjunction with the PARP inhibitor (PARPi) or a platin analog therapy. In some aspects, the anti-cancer therapy is chemotherapy, immunotherapy, surgery, radiotherapy, or biotherapy. The second anti-cancer therapy may be a PKCβ inhibitor, such as Enzastaurin (LY317615). In other aspects, the second anti-cancer therapy may comprise a TTK inhibitor, mTOR inhibitor, or a PI3K inhibitor. The PARP inhibitor, cisplatin, and/or at least a second anti-cancer therapy are administered orally, intravenously, intraperitoneally, intratracheally, intratumorally, intramuscularly, endoscopically, intralesionally, percutaneously, subcutaneously, topically, regionally, or by direct injection or perfusion. The PARP inhibitor, cisplatin and/or at least a second anti-cancer therapy may be administered simultaneously or the PARP inhibitor or cisplatin may be administered prior to or after the second anti-cancer therapy.

In certain aspects of the present methods, the cancer may be a renal cancer, a lung cancer, an ovarian cancer, or a breast cancer. In some aspects, the cancer is a BRCA mutant cancer regardless of tissue of origin. In other aspects, the cancer is a BRCA wild-type cancer.

In one embodiment, the present disclosure provides a composition comprising a PARP inhibitor or platin analog for use in treating a cancer patient determined to have a DNA repair (e.g., HR repair) defective cancer. In certain aspects of the present methods, the cancer may be a renal cancer, a lung cancer, an ovarian cancer, or a breast cancer. In some aspects, the cancer is a BRCA mutant cancer regardless of tissue of origin. In other aspects, the cancer is a BRCA wild-type cancer. In certain aspects, the method may further comprise administering a second anti-cancer therapy to the subject in conjunction with the PARP inhibitor or a platin analog therapy. The second anti-cancer therapy may be a PKCβ inhibitor, such as Enzastaurin (LY317615). In further aspects, the second anti-cancer therapy may comprise a TTK inhibitor, mTOR inhibitor, or a PI3K inhibitor. In particular aspects, a PARP inhibitor or PARP inhibitor-based anticancer therapy may comprise olaparib, ABT-888 (Veliparib), BMN 673, Iniparib (BSI-201), Rucaparib (AG-014699, PF-01367338), AG14361, INO-1001, A-966492, PJ34, or MK-4827.

In one embodiment, the present disclosure provides a composition comprising a PKCβ inhibitor and a PARP inhibitor for use in treating a cancer in a patient. In some aspects, the PARP inhibitor or PARP inhibitor-based anticancer therapy may comprise olaparib, ABT-888 (Veliparib), BMN 673, Iniparib (BSI-201), Rucaparib (AG-014699, PF-01367338), AG14361, INO-1001, A-966492, PJ34, or MK-4827. In certain aspects, the PKCβ inhibitor is Enzastaurin (LY317615).

In still a further embodiment, the present disclosure provides a method of sensitizing a cancer to a PARP inhibitor-based anticancer therapy comprising administering an effective amount of a PKCβ inhibitor to a patent having the cancer. The method may further comprise administering a PARP inhibitor-based anticancer therapy to the subject. In another aspect, the PARP inhibitor-based anticancer therapy may be administered essentially simultaneously with said PKCβ inhibitor.

In another embodiment, there is provided a method of treating cancer in a subject comprising obtaining a sample comprising cancer cells; measuring the expression levels of at least 3 genes selected from the group consisting of genes in Table 1 or Table 2 in the sample to obtain relative gene fold changes; determining a signature score from the relative gene fold changes, wherein the subject has therapy sensitive cancer if the signature score is above a threshold level; and administering an effective amount of a PARP inhibitor and/or platin analog therapy to the subject identified to have an therapy sensitive cancer. In some aspects, the threshold is determined relative to a healthy subject. In certain aspects, the signature score is determined following normalization to reference genes. In particular aspects, the platin analog therapy is cisplatin. In some aspects, the subject is human.

In some aspects, determining the signature score comprises taking the spearman correlation coefficient between the gene expression values. In certain aspects, determining the signature score comprises multiplying each relative gene fold change by coefficients from the gene signature and summing values to obtain a signature score.

In certain aspects, the sample is blood, saliva, urine, or a tissue biopsy. In some aspects, the method further comprises isolating RNA from the sample. In some aspects, measuring the expression levels comprises preforming RT-PCR, a hybridization, transcriptome analysis, a Northern blot, a Western blot, RNA sequencing, or an ELISA.

In some aspects, the method further comprises measuring the expression levels of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, or 147 of the genes listed in Table 1. In certain aspects, the method may comprise measuring the expression levels of at least 4, 5, 6, 7, 8, 9, 10, 11, 12, 13, 14, 15, 16, 17, 18, 19, 20, 21, 22, 23, 24, 25, or 26 of the genes listed in Table 2. In some aspects, at least one of the genes is a gene from Table 1A or Table 2A and the cancer is identified as therapy sensitive (e.g., PARP inhibitor or platinum-based therapy sensitive) if the gene is up-regulated relative to a control expression level; or the cancer is identified as therapy resistant if the gene is not up-regulated relative to a control expression level. In certain aspects, at least one of the genes is a gene from Table 1B or Table 2B and the cancer is identified as therapy sensitive if the gene is down-regulated relative to a control expression level; or the cancer is identified as therapy resistant if the gene is not down-regulated relative to a control expression level.

In particular aspects, the method further comprises administering at least a second anti-cancer therapy. In some aspects, the anti-cancer therapy is chemotherapy, immunotherapy, surgery, radiotherapy, or biotherapy. In certain aspects, the PARP inhibitor, platin analog, and/or at least a second anti-cancer therapy are administered orally, intravenously, intraperitoneally, intratracheally, intratumorally, intramuscularly, endoscopically, intralesionally, percutaneously, subcutaneously, topically, regionally, or by direct injection or perfusion. In certain aspects, the PARP inhibitor, platin analog and/or at least a second anti-cancer therapy are administered simultaneously. In some aspects, the PARP inhibitor and/or platin analog is administered prior to the at least a second anti-cancer therapy. In particular aspects, the anti-cancer therapy is a PKCβ inhibitor, such as Enzastaurin (LY317615).

A kit for determining the expression levels of at least 3 of the therapy predictive genes of Table 1 or Table 2 in a sample comprising primers that recognize each of the at least 3 genes or an array comprising said primers; and instructions for performing a method for determining the expression levels of said therapy predictive genes. The kit may comprise further reagents for determining the expression levels of the therapy predictive genes.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) 857 solid-tumor cancer cells were stochastically and iteratively sampled for pharmaceutical agent sensitivity or insensitivity determination. Differential expression for the combination of two therapeutic agents per target was calculated. This process was repeated 1000 times for the generation of 1000 different lists of differentially expressed genes. Optimization of the final signature included maximization of accuracy on the tissue of interest by selecting optimal thresholds of P-values and fold changes that were represented in a given fraction of the iterations. (FIG. 1B) Receiver-operating characteristic (ROC) curves for the prediction of training sets with the HER2 inhibitor Afatinib in breast cancer cell lines with inset accuracy and inset with area under the curve (AUC) values. A ROC AUC value of 1 represents perfect prediction and 0.5 represents random chance. (FIG. 1C) ROC curve for predicting HER2/Erbb2 patients based on the HER2i sensitivity score.

FIGS. 2A-2G: The cisplatin sensitivity signature that was generated from IRAPS predicts cisplatin-treated ovarian cancer patient survival independent of cancer stage and grade. (FIG. 2A) ROC curve based on the cisplatin sensitivity score using the cisplatin testing set that consisted of triple-negative breast cancer and ovarian cancer cell lines. (FIG. 2B) ROC curve for the same cells as in 2A, but based on the BRCAness sensitivity signature score. (FIGS. 2C-2D) Patient survival analyses in two independent cohorts of ovarian cancer patients that were treated with cisplatin were separated based on the cisplatin sensitivity score. Log-rank p-value is displayed that shows statistical significance. Signature-negative showed lower percent survival. (FIGS. 2E-2F) High cisplatin sensitivity scores predict improved overall survival (FIG. 2E) and progression free survival (FIG. 2F) independent of stage and grade using a Cox proportional hazards model. Signature negative showed lower percent survival. (FIG. 2G) Ingenuity pathway analysis of the cisplatin sensitivity signature indicates a predicted down-regulation of BRCA1.

(FIGS. 3A-3B) Screening results for sensitivity to PARP inhibitor BMN-673 in breast (FIG. 3A) and ovarian (FIG. 3B) cancer cell lines. (FIGS. 3C-3D) AUC values from ROC curves (FIG. 3C) and overall accuracy (FIG. 3D) (top:ovarian; bottom: breast) for prediction of sensitivity to the PARP inhibitor BMN-673 in ovarian and breast cancer cell lines determined based on BRCAness score and PARP sensitivity score, as well as by directly using the COSMIC IC50 values for AZD2281 (olaparib) and AG014699 (rucaparib) from which the PARP sensitivity signature was derived as an achievable upper bound. Overall accuracy was also analyzed based on BRCA1/2 mutation status. (FIG. 3E) ROC curves for prediction of primary patient-derived tumor cells (PDTCs) 30 response to BMN-673 shows PARPi sensitivity signature outperforms BRCAness signature. (FIG. 3F) Accuracy of predicting PARPi sensitivity for PTDCs based on PARPi sensitivity score, BRCAness score, and BRCA1/2 mutation status. (FIGS. 3G-3I) Growth curves for breast cancer PDXs with low (FIG. 3G), moderate (FIG. 3H), and high (FIG. 3I) PARPi sensitivity scores following treatment with the PARP inhibitor AZD2281 QD at 50 mg/kg. (FIG. 3J) Ratio of tumor volumes in AZD2281-treated versus vehicle controls. Ratios were calculated on day 15 and plotted as a function of the PARPi sensitivity score, demonstrating a strong negative correlation.

(FIGS. 4A-4E) Viability curves following BMN673 treatment with or without the PKCβ inhibitor LY317615 at a constant molar ratio of 1:3 BMN673:LY317615 for 5 days in the breast cancer cells (FIG. 4A) MDA-MB-231, and (FIG. 4B) MCF7, and in the ovarian cancer cell lines (FIG. 4C) ES2 and (FIG. 4D) BRCA-mutant COV362, as well as in the (FIG. 4E) non-transformed mammary epithelial cell line MCF10A. (FIG. 4F) Isobolograms calculated at IC50 values for cancer cell lines demonstrate synergism for all analyzed lines. (FIG. 4G) Combination indices demonstrate synergism between PARPi and PKCβi in a panel of ovarian and breast cancer cell lines across a range of inhibitor concentrations.

(FIG. 5A) DR-GFP homologous recombination (HR) reporter assay, where GFP induction is induced in cells with active HR following dual transfection with the DR-GFP and the pCBA-SceI. The day after transfection, cells were treated with either 5 μM LY317615 (right) or DMSO (left) vehicle control for 48 hours. The percentage of cells with active HR was calculated as the percentage of DR-GFP positive cells normalized to percentage GFP positive cells transfected with an equimolar amount of pEGFP-C1. (FIG. 5B) Reduction in radiation-induced Rad51 foci formation shows inhibited HR. Cells were pre-treated with 5 NM LY317615 for 4 hours, irradiated at 5 Gy, and then allowed to recover for 4 hours before immunostaining for Rad51 (red) and nuclei (blue). Scale bar=10 μm. (FIG. 5C) Quantification of images in 5B, when considering that cells with more than 10 Rad51 foci are deemed as being positive.

(FIG. 6A) Volcano plot of compounds predicted to target BRCA-like cells based on the BRCAness signature score. (FIG. 6B) Viability curves following 72 hours of treatment with identified BRCAness-targeting molecules for BRCA1 mutant COV362, BRCA-like A2780, and non-BRCA-like ES2 and OVCAR8. (FIG. 6C) Viability curves following 72 hours of treatment with drugs that BRCA-like cells are predicted to be resistant to.

(FIG. 9A-B) Dose-response curves for cells treated with BMN-673 in combination with Cucurbitacin I, which was predicted reverse the PARPi sensitivity signature. Cuc+BMN or Cuc showed decreased percent viability. (BMN:square; Cuc+BMN:triangle; Cuc: circle) (FIG. 9C) Quantification of combination index from $IC_{50}$ values shows significant antagonism (combination index >1) in ES2 ovarian cancer cells and no interaction in COV362. * indicates significantly antagonistic, p<0.01.

(FIG. 10A) Images of radiation-induced Rad51 foci formation. Cells were pre-treated with 5 μM LY317615 for 4 hours, irradiated at 5 Gy, and then allowed to recover for 4 hours before immunostaining for Rad51 and nuclei. Scale bar=10 μm. (FIG. 10B) Quantification of images in A, when considering that cells with more than 10 Rad51 foci are deemed as being positive.

DESCRIPTION OF ILLUSTRATIVE EMBODIMENTS

Figure 1A:
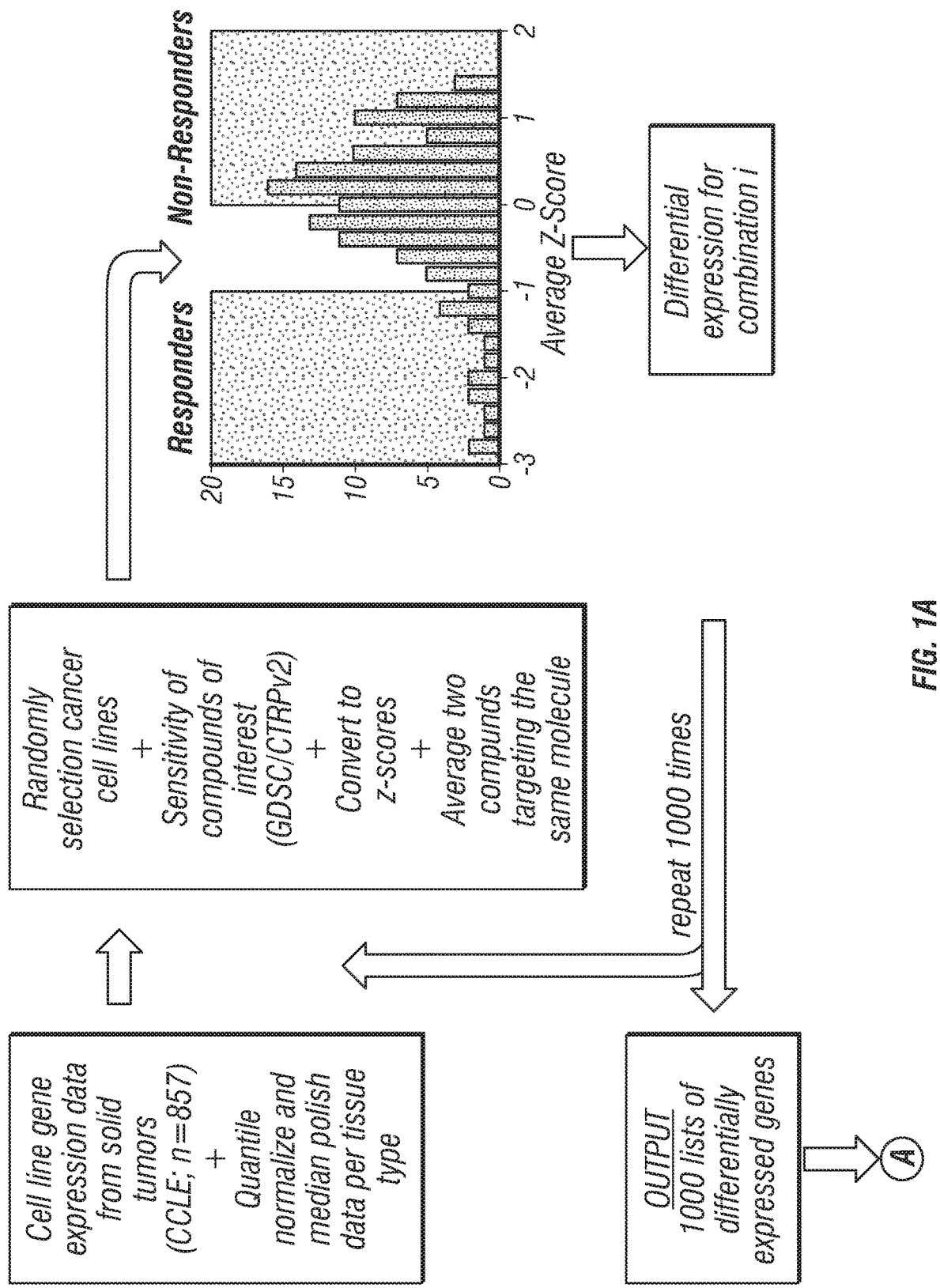
FIGS. 1A-1C: Overview of iterative resampling analysis to predict sensitivity (IRAPS).
Figure 1A:
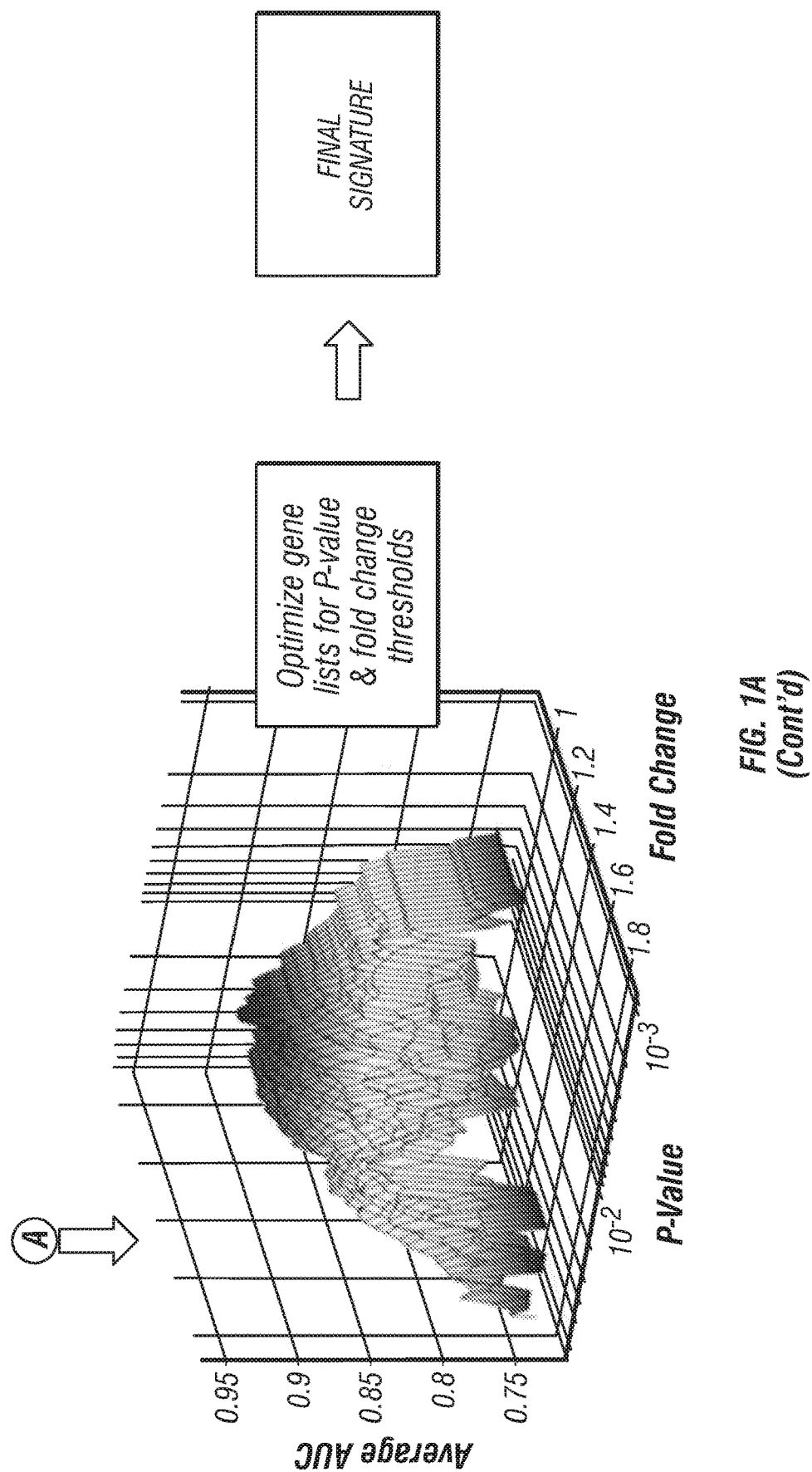

Despite rapid advancement in generation of large-scale microarray gene expression datasets, robust multigene expression signatures that are capable of guiding the use of specific therapies have not been routinely implemented into clinical care. The present disclosure provides, in certain embodiments, an iterative resampling analysis to predict sensitivity (IRAPS) algorithm to generate gene expression sensitivity profiles that predict patient responses to specific therapies. The resultant signatures provided herein have a robust capacity to accurately predict drug sensitivity, such as cisplatin and poly (ADP-ribose) polymerase (PARP) inhibitors, as well as the identification of synergistic combinations.

The present studies used the novel IRAPS algorithm to develop gene expression signatures to predict response to PARP inhibition as well as to the chemotherapy agent cisplatin. This algorithm integrates gene expression data from hundreds of solid tumor cell lines with known sensitivity to pharmaceutical agents. This broad panel of cell lines was randomly sampled over 1000 iterations to determine differentially expressed genes, before final optimization of the signature on the desired cancer type. In addition to demonstrating high accuracy in cell line panels, these signatures were capable of predicting patient survival following cisplatin treatment and response of both primary patient-derived tumor cells (PTDCs) and patient-derived xenografts (PDXs) to PARP inhibition.

Specifically, the IRAPS approach was applied to predict response to PARP inhibitors, and was shown to greatly outperform current clinical biomarkers, including BRCA1/2 mutation status, accurately identifying PARP inhibitor-sensitive cancer cell lines, primary patient-derived tumor cells, and patient-derived xenografts. These signatures were also capable of predicting patient response, as shown by applying a cisplatin sensitivity signature to ovarian cancer patients. In addition, these drug-sensitivity signatures were applied to identify novel synergizing agents to improve drug efficacy. Finally, it was demonstrated how documented gene expression signatures can be leveraged to identify therapeutic targets for previously known molecular phenotypes such as BRCAness. Taken together, this work provides a method for development of robust actionable gene expression signatures capable of improving clinical patient outcomes. Thus, certain embodiments of the present disclosure provide methods to tailor therapeutic interventions to improve patient prognosis.

I. DEFINITIONS

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

"Prognosis" refers to as a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis and/or cancer progression in a patient susceptible to or diagnosed with a cancer. Prognosis also includes prediction of favorable survival following cancer treatments, such as a conventional cancer therapy.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The term "immune checkpoint" refers to a molecule such as a protein in the immune system which provides signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

The term "determining an expression level" or "measuring an expression level" as used herein means the application of a gene specific reagent such as a probe, primer or antibody and/or a method to a sample, for example a sample of the subject and/or a control sample, for ascertaining the measuring quantitatively, semi-quantitatively or qualitatively the amount of a gene or genes, for example the amount of mRNA. For example, a level of a gene can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR, serial analysis of gene expression (SAGE), Northern Blot, digital molecular barcoding technology, for example Nanostring:nCounter™ Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene®ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and for example for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by fine needle aspiration that is directed to a target, such as a tumor, or is random sampling of normal cells, such as periareolar), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet. In some embodiments, the sample is a formalin fixed paraffin embedded (FFPE) tumor tissue sample, e.g., from a solid tumor of the breast.

The term "altered" refers to a gene that is present at a detectably up-regulated or down-regulated level in a biological sample, e.g. plasma, from a patient with cancer, in comparison to a biological sample from a patient without cancer. The term includes increased or decreased expression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer. Altered expression can be 10%, 20%, 30%, 40%, 50%, 60%, 70%, 80%, 90% or more in comparison to a sample from a patient without cancer.

The terms "increased", "elevated", "overexpress", "overexpression", "overexpressed", "up-regulate", or "up-regulated" interchangeably refer to a gene that is present at a detectably greater level in a biological sample, e.g. plasma, from a patient with cancer, in comparison to a biological sample from a patient without cancer. The term includes overexpression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer. Overexpression can be detected using conventional techniques for detecting mRNA (i.e., RT-PCR, PCR, hybridization) or proteins (i.e., ELISA, immunohistochemical techniques, mass spectroscopy, Luminex® xMAP technology). Overexpression can be 10%, 20%, 30%, 40%, 50%, 60%, 70%, 80%, 90% or more in comparison to a sample from a patient without cancer. In certain instances, overexpression is 1-fold, 2-fold, 3-fold, 4-fold 5, 6, 7, 8, 9, 10, or 15-fold or more higher levels of transcription or translation in comparison to a sample from a patient without cancer.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in Harrison's Principles of Internal Medicine, Kasper, et al., eds., 16th ed., 2005, Chapter 70, and throughout Part V. One skilled in the art will appreciate that biopsy techniques can be performed to identify cancerous and/or precancerous cells in a given tissue sample.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

II. GENE SIGNATURES PREDICTIVE OF DRUG RESPONSE

Certain embodiments of the present disclosure provide a gene signature to predict sensitivity to drugs, including anti-cancer agents such as cisplatin and PARP inhibitors. Thus, some aspects concern the detection and quantification of certain genes in a sample. The PARPi gene signature comprises a combination of genes disclosed in Table 1 which predict response to a PARP inhibitor. In some aspects, 3, 4, 5, 6, 7, 8, 9, 10, 11, 12, 13, 14, 15, 16, 17, 18, 19, 20, 25, 30, 40, 50, 75, 100, 125, 140 or more of the genes in Table 1 are used to determine the response to PARP inhibition. The PARPi signature genes can be normalized to reference genes. In other aspects, response to cisplatin is determined using 3, 4, 5, 6, 7, 8, 9, 10, 11, 12, 13, 14, 15, 16, 17, 18, 19, 20, 21, 22, 22, 23, 24, 25, or 26 of the genes in Table 2.

TABLE 1

PARPi sensitivity gene signature.

| Gene | Fold Change |
|---|---|
| A: Up-regulated genes | |
| SNX10 | 2.10294 |
| ECI2 | 1.59528 |
| DBN1 | 1.55135 |
| TNFRSF10B | 1.53927 |
| NPM3 | 1.52744 |
| CATSPER1 | 1.51482 |
| PRMT3 | 1.47361 |
| FAM216A | 1.46995 |
| LYAR | 1.46464 |
| NOP16 | 1.43368 |
| THG1L | 1.43165 |
| LOC439949 | 1.41824 |
| TMA16 | 1.37999 |
| GEMIN4 | 1.36272 |
| HAUS6 | 1.35154 |

TABLE 1-continued

PARPi sensitivity gene signature.

| Gene | Fold Change |
|---|---|
| SFXN4 | 1.34349 |
| SAAL1 | 1.3368 |
| NUP160 | 1.32974 |
| ESD | 1.32843 |
| TSEN15 | 1.32454 |
| KIAA1704 | 1.30893 |
| HSPA4 | 1.30871 |
| SFXN1 | 1.30228 |
| NAT10 | 1.29537 |
| C11orf48 | 1.29247 |
| TSEN2 | 1.29095 |
| HEATR2 | 1.28768 |
| GEMIN5 | 1.28744 |
| IMPDH2 | 1.28697 |
| NOC3L | 1.28663 |
| ERLIN1 | 1.28312 |
| C1QBP | 1.27993 |
| EIF3M | 1.27516 |
| MTHFD1L | 1.27356 |
| MTX3 | 1.2713 |
| MRPS27 | 1.26203 |
| PPRC1 | 1.25793 |
| TCOF1 | 1.25381 |
| IDE | 1.25345 |
| RNF2 | 1.24787 |
| WDR75 | 1.24375 |
| NAA15 | 1.24202 |
| DDX21 | 1.24141 |
| RARS | 1.23722 |
| ALG8 | 1.22804 |
| BOLA3 | 1.22746 |
| EARS2 | 1.21638 |
| FAF2 | 1.21516 |
| MRPL42 | 1.2047 |
| ATIC | 1.20415 |
| NUP37 | 1.20075 |
| RPL36 | 1.17599 |
| GNB2L1 | 1.10048 |
| B: Down-regulated genes | |
| NPBWR1 | −1.08727 |
| GALNTL5 | −1.09057 |
| LOC729173 | −1.1028 |
| LOC441461 | −1.11147 |
| KALRN | −1.11385 |
| ADCY2 | −1.12115 |
| MTHFR | −1.12877 |
| MS4A7 | −1.13092 |
| RNF186 | −1.1328 |
| IRF4 | −1.13719 |
| WBSCR17 | −1.13942 |
| CLEC7A | −1.13998 |
| WDTC1 | −1.14431 |
| PRKG2 | −1.15777 |
| OSTalpha | −1.15949 |
| DUSP18 | −1.16187 |
| LOC100652843 | −1.1619 |
| FAIM2 | −1.16224 |
| TNNI2 | −1.16606 |
| SEZ6 | −1.17205 |
| LOC285556 | −1.17822 |
| KCNQ1 | −1.17832 |
| KLF8 | −1.18448 |
| VPS13D | −1.18989 |
| NR0B2 | −1.19007 |
| TMEM86A | −1.19621 |
| DCAF5 | −1.19867 |
| SOS2 | −1.19921 |
| CAPN9 | −1.19996 |
| RIPK3 | −1.20212 |
| TPRXL | −1.20512 |
| CELF4 | −1.21076 |
| ATP6V1E1 | −1.22087 |
| ZBTB7C | −1.22788 |
| CATSPERB | −1.23469 |
| CAPN13 | −1.23914 |

TABLE 1-continued

PARPi sensitivity gene signature.

| Gene | Fold Change |
| --- | --- |
| MMEL1 | −1.23986 |
| ELF5 | −1.24888 |
| C2orf54 | −1.25498 |
| DVL3 | −1.25615 |
| SIRT2 | −1.26055 |
| LOC641518 | −1.26063 |
| IL12RB2 | −1.26353 |
| CBFA2T2 | −1.265 |
| LINC00518 | −1.27029 |
| OSBPL2 | −1.27479 |
| SH3GLB1 | −1.27511 |
| CHMP4B | −1.2759 |
| HSD11B2 | −1.28337 |
| ACVR1C | −1.28707 |
| TMEM61 | −1.29722 |
| DLL3 | −1.30821 |
| CXCL17 | −1.31493 |
| SLC44A4 | −1.32005 |
| RNF183 | −1.32362 |
| KLK8 | −1.33067 |
| RIIAD1 | −1.34559 |
| ATP7A | −1.34616 |
| GJB1 | −1.34986 |
| BCAS1 | −1.36267 |
| SCGN | −1.37289 |
| TTC3 | −1.37453 |
| IGSF11 | −1.38772 |
| LOC440335 | −1.39406 |
| LOC645591 | −1.44501 |
| C4orf3 | −1.44729 |
| LRRC31 | −1.46158 |
| ADAM12 | −1.48037 |
| BHLHE41 | −1.48707 |
| RNASE1 | −1.49348 |
| PPP1R3B | −1.4951 |
| LOC100505989 | −1.51135 |
| CAPN8 | −1.51278 |
| C2CD4A | −1.51447 |
| CHGA | −1.52108 |
| ERBB2 | −1.52264 |
| NELL1 | −1.53281 |
| FAM174B | −1.58523 |
| CALML5 | −1.58896 |
| TSC22D3 | −1.58913 |
| C9orf152 | −1.60047 |
| KLK6 | −1.60833 |
| MB | −1.61385 |
| ST6GALNAC1 | −1.62347 |
| SFTA2 | −1.65345 |
| MUC1 | −1.71504 |
| SETBP1 | −1.80665 |
| SCG3 | −1.83905 |
| PRUNE2 | −1.8717 |
| SSPN | −1.8783 |
| CEACAM5 | −1.89571 |
| TMEM45B | −1.91414 |
| MAFB | −1.9233 |
| ZNF880 | −1.92673 |

TABLE 2

Cisplatin sensitivity gene signature.

| Gene | Fold Change |
| --- | --- |
| A: Up-regulated genes | |
| DUSP6 | 3.49732 |
| ETV4 | 2.16731 |
| ERBB2 | 2.12724 |
| GAMT | 1.7727 |
| EXOC6 | 1.61206 |
| SS18 | 1.60988 |

TABLE 2-continued

Cisplatin sensitivity gene signature.

| Gene | Fold Change |
| --- | --- |
| CASP3 | 1.59993 |
| DSCC1 | 1.5846 |
| FOXO3 | −1.57637 |
| ARHGEF18 | −1.58661 |
| EVPL | −1.59421 |
| ERCC1 | −1.63353 |
| C5orf51 | −1.67628 |
| ADAMTS15 | −1.71242 |
| RNASET2 | −1.71603 |
| PRR16 | −1.72416 |
| ANKRD13A | −1.7311 |
| RASD1 | −1.74297 |
| COL6A1 | −1.86589 |
| COL4A6 | −2.03089 |
| PARP9 | −2.04978 |
| MN1 | −2.42967 |
| HORMAD1 | −2.81595 |
| SERPINB5 | −3.26972 |
| MAL2 | −3.46299 |
| KRT17 | −5.33673 |
| B: Down-regulated genes | |
| FOXO3 | −1.57637 |
| ARHGEF18 | −1.58661 |
| EVPL | −1.59421 |
| ERCC1 | −1.63353 |
| C5orf51 | −1.67628 |
| ADAMTS15 | −1.71242 |
| RNASET2 | −1.71603 |
| PRR16 | −1.72416 |
| ANKRD13A | −1.7311 |
| RASD1 | −1.74297 |
| COL6A1 | −1.86589 |
| COL4A6 | −2.03089 |
| PARP9 | −2.04978 |
| MN1 | −2.42967 |
| HORMAD1 | −2.81595 |
| SERPINB5 | −3.26972 |
| MAL2 | −3.46299 |
| KRT17 | −5.33673 |

In one method, the gene expression values may be analyzed by taking the correlation coefficient (i.e., spearman) between the gene expression values to obtain signature coefficients (see, for example, U.S. Pat. No. 8,019,5521; incorporated herein by reference). In one embodiment, the similarity of said expression profile to a HR defective or not HR defective is represented by a correlation coefficient between said expression profile, and a correlation coefficient greater than a correlation threshold, e.g., 0.2 (or 0.3, 0.4, 0.5, 0.6, or higher), indicates a high similarity and said correlation coefficient equal to or less than said correlation threshold indicates a low similarity.

In another method, the gene expression values may be used to generate a weighted "signature score." For example, each relative gene fold change may be multiplied by the coefficient from the gene signature and then the sum of these values taken as a signature score. This score may then be normalized to the sum of the absolute values of the coefficients.

A. Isolation of RNA

Aspects of the present disclosure concern the isolation of RNA from a patient sample for use in determining the expression level of a drug sensitivity gene signature, such as the PARP inhibitor signature. The patient sample may blood, saliva, urine, or a tissue biopsy. The tissue biopsy may be a tumor biopsy that has been flash-frozen (e.g. in liquid nitrogen), formalin-fixed and paraffin-embedded (FFPE), and/or preserved by a RNA stabilization agent (e.g., RNAlater). In some aspects, isolation is not necessary, and the assay directly utilizes RNA from within a homogenate of the tissue sample. In certain aspects the homogenate of FFPE tumor sample is enzymatically digested.

RNA may be isolated using techniques well known to those of skill in the art. Methods generally involve lysing the cells with a chaotropic (e.g., guanidinium isothiocyanate) and/or detergent (e.g., N-lauroyl sarcosine) prior to implementing processes for isolating particular populations of RNA. Chromatography is a process often used to separate or isolate nucleic acids from protein or from other nucleic acids. Such methods can involve electrophoresis with a gel matrix, filter columns, coated magnetic beads, alcohol precipitation, and/or other chromatography.

B. Expression Assessment

In certain aspects, methods of the present disclosure concern measuring expression of PARP inhibitor signature genes as well as one or more reference genes in a sample from a subject with cancer, such as breast cancer or ovarian cancer. The expression information may be obtained by testing cancer samples by a lab, a technician, a device, or a clinician. In a certain embodiment, the differential expression of one or more genes including those of Table 1 may be measured.

Expression levels of the genes can be detected using any suitable means known in the art. For example, detection of gene expression can be accomplished by detecting nucleic acid molecules (such as RNA) using nucleic acid amplification methods (such as RT-PCR, droplet-based RT amplification, exon capture of RNA sequence library, next generation RNA sequencing), array analysis (such as microarray analysis), or hybridization methods (such as ribonuclease protection assay, bead-based assays, or Nanostring®). Detection of gene expression can also be accomplished using assays that detect the proteins encoded by the genes, including immunoassays (such as ELISA, Western blot, RIA assay, or protein arrays).

The pattern or signature of expression in each cancer sample may then be used to generate a cancer prognosis or classification, such as predicting cancer survival or recurrence, using the PARP inhibitor gene signature. The expression of one or more of the PARP inhibitor genes could be assessed to predict or report prognosis or prescribe treatment options for cancer patients, especially breast cancer patients.

The expression of one or more the genes may be measured by a variety of techniques that are well known in the art. Quantifying the levels of the messenger RNA (mRNA) of a gene may be used to measure the expression of the gene. Alternatively, quantifying the levels of the protein product of PARP inhibitor-related genes may be to measure the expression of the genes. Additional information regarding the methods discussed below may be found in Ausubel et al., (2003) Current Protocols in Molecular Biology, John Wiley & Sons, New York, N.Y., or Sambrook et al. (1989) Molecular Cloning: A Laboratory Manual, Cold Spring Harbor Press, Cold Spring Harbor, N.Y. One skilled in the art will know which parameters may be manipulated to optimize detection of the mRNA or protein of interest.

A nucleic acid microarray may be used to quantify the differential expression of a plurality of genes. Microarray analysis may be performed using commercially available equipment, following manufacturer's protocols, such as by using the Affymetrix GeneChip® technology (Santa Clara, Calif.) or the Microarray System from Incyte (Fremont, Calif.). Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with a robust statistical normalization algorithm to generate expression values.

Quantitative real-time PCR (qRT-PCR) may also be used to measure the differential expression of a plurality of genes. In qRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

For example, extracted RNA can be reverse-transcribed using a GeneAmp® RNA PCR kit (Perkin Elmer, Calif., USA), following the manufacturer's instructions. In some embodiments, gene expression levels can be determined using a gene expression analysis technology that measure mRNA in solution. Methods of detecting gene expression are described for example in U.S. Patent Application Nos. US20140357660, and US20130259858; incorporated herein by reference. Examples of such gene expression analysis technologies include, but not limited to RNAscope™, RT-PCR, Nanostring®, QuantiGene®, gNPA®, HTG®, microarray, and sequencing. For example, methods of Nanostring use labeled reporter molecules, referred to as labeled "nanoreporters," that are capable of binding individual target molecules. Through the nanoreporters' label codes, the binding of the nanoreporters to target molecules results in the identification of the target molecules. Methods of Nanostring are described in U.S. Pat. No. 7,473,767. Methods may include the RainDance droplet amplification method such as described in U.S. Pat. No. 8,535,889, incorporated herein by reference. Sequencing may include exon capture, such as Illumina targeted sequencing after the generation of a tagged library for next generation sequencing (e.g. described in International Patent Application No. WO2013131962, incorporated herein by reference).

A non-limiting example of a fluorescent reporter probe is a TaqMan® probe (Applied Biosystems, Foster City, Calif.). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, qRT-PCR is typically performed using a reference standard. The ideal reference standard is expressed at a constant level among different tissues, and is unaffected by the experimental treatment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems (Foster City, Calif.).

The steps of a representative protocol for quantitating gene expression level using fixed, paraffin-embedded tissues as the RNA source, including mRNA isolation, purification, primer extension and amplification are known in the art. Briefly, a representative process starts with cutting about 10μm thick sections of paraffin-embedded neoplasm tissue samples or adjacent non-cancerous tissue. The RNA is then extracted, and protein and DNA are removed. Alternatively, RNA is isolated directly from a neoplasm sample or other tissue sample. After analysis of the RNA concentration, RNA repair and/or amplification steps can be included, if necessary, and RNA is reverse transcribed using gene specific primers, followed by preparation of a tagged RNA sequencing library, and paired-end sequencing. In another example, the RNA is not reverse transcribed, but is directly hybridized to a specific template and then labeled with oligonucleotides and/or chemical or fluorescent color to be detected and counted by a laser.

Immunohistochemical staining may also be used to measure the differential expression of a plurality genes. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the gene.

An enzyme-linked immunosorbent assay, or ELISA, may be used to measure the differential expression of a plurality of genes. There are many variations of an ELISA assay. All are based on the immobilization of an antigen or antibody on a solid surface, generally a microtiter plate. The original ELISA method comprises preparing a sample containing the proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of a plurality of genes. For this, a plurality of antibodies is arrayed and covalently attached to the surface of the microarray or biochip. A protein extract containing the proteins of interest is generally labeled with a fluorescent dye.

The labeled proteins may be incubated with the antibody microarray. After washes to remove the unbound proteins, the microarray is scanned. The raw fluorescent intensity data may be converted into expression values using means known in the art.

Luminex multiplexing microspheres may also be used to measure the differential expression of a plurality of genes. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., mRNA or protein, respectively). The target, in turn, is also tagged with a fluorescent reporter. Hence, there are two sources of color, one from the bead and the other from the reporter molecule on the target. The beads are then incubated with the sample containing the targets, of which up 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of genes. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each gene.

C. Methods of Use

Aspects of the present disclosure include methods for predicting the response of cancer in a subject to an anti-cancer agent by, for example, obtaining cell or tissue samples from a subject and determining such samples for the presence of altered expression of the genes in the drug response signatures provided herein. As used herein, the term "cancer" refers to an uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. In particular embodiments, a subject who is diagnosed or treated by the present methods, is a subject with breast cancer or ovarian cancer.

The methods described herein can be used to screen patients for response to certain anti-cancer agents, such as PARP inhibitors. The methods described herein can be used alone, or in conjunction with other tests. In general, microarray analysis is performed on a plasma sample, and the altered expression of the gene signature is determined. Patients that have altered expression of signature genes receive appropriate treatment.

III. METHODS OF TREATING

Certain aspects of the present disclosure can be used to identify, delay progression and/or treat a disease or disorder, such as cancer, based on the presence of a gene signature provided herein. Other aspects of the present disclosure provide for sensitizing a subject with cancer to treatment with PARP inhibitors. The therapy, such as a PARP inhibitor, may be used in a maintenance setting, such as to help prevent recurrence after a subject is treated with a primary course of chemotherapy.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

The methods described herein are useful in treating cancer, particularly, homologous recombination deficient cancer. More specifically, cancers that are treated using any one or more PARP inhibitors, or variants thereof, and in connection with the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo maligna melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Poly(ADP-ribose)polymerase has an essential role in facilitating DNA repair, controlling RNA transcription, mediating cell death, and regulating immune response. PARP inhibitors are a group of pharmacological inhibitors of the enzyme PARP. In various preclinical cancer models and human clinical trials, PARP inhibitors have been shown to potentiate radiation and chemotherapy by increasing apoptosis of cancer cells, limiting tumor growth, decreasing metastasis, and prolonging the survival of tumor-bearing subjects. (WO 2007/084532; Donawho et al., 2007; Kummar et al., 2009). By way of example, PARP inhibitors include, but are not limited to, olaparib (AZD-2281), veliparib (ABT-888), iniparib (BSI-201), rucaparib (AG014699, PF-01367338), AG14361, INO-1001, A-966492, PJ34, MK-4827, CEP 9722, BMN-673, 3-aminobenzamide, niraparib, and those disclosed in U.S. Pat. Nos. 7,928,105; 8,124,606; 8,236,802; 8,450,323; WO 2006/110816; WO 2008/083027; and WO 2011/014681.

In some aspects, the PARP inhibitor may be combined with a TTK inhibitor, a mTOR inhibitor, and/or a PI3K inhibitor. The PARP inhibitor may be combined with an ATR inhibitor (e.g., ZD6738), a CHK1/2 inhibitor, a MEK inhibitor, BRD4 inhibitor, and/or an immunotherapy.

TTK, a dual serine-threonine kinase involved in mitotic spindle assembly checkpoint, is encoded by the human protein kinase monopolar spindle 1 (hMps 1/TTK) gene. By way of example, TTK inhibitors include, but are not limited to, MPI-0479605, AZ3146, and those disclosed in US2003/0045491; US2011/0002923; WO 2009/024824; WO2010/007756; WO 2011/064328; WO 2011/063907; and WO 2011/063908.

Mammalian target of rapamycin (mTOR) is a serine/threonine kinase, which belongs to the phosphatidylinositol-3 kinase (PI3K) related kinases (PIKKs) family. It regulates cellular metabolism, growth, and proliferation. An mTOR inhibitor may be an allosteric or catalytic inhibitor. By way of example, mTOR inhibitors include, but are not limited to, OSI-027, rapamycin, sirolimus, deforolimus (AP23573), everolimus (RAD001), temsirolimus (CCI-779), INK128; OXA-01 (OSI-950), PP-242, PP-30, AZD2014; AZD8055, INK-128, Torin-1, WYE-132, GSK-2126458, and those disclosed in US 2007/0112005; US 2010/0048547; WO2010/006072; US 2009/0312319; US 2010/0015140; US 2007/0254883; US 2007/0149521.

A Phosphoinositide 3-kinase inhibitor (PI3K inhibitor) is a drug that functions by inhibiting a PI3K, which, through inhibition, often results in tumor suppression. By way of example, PI3K inhibitors include, but are not limited to LY-294002, wortmannin, BKM120, demethoxyviridin, perifosine; PX-866; IPI-145; BAY 80-6946; idelalisib; BEZ235; BYL 719; RP6530; TGR 1202; INK1117; GDC-0941; GDC-0980; XL147; XL765; palomid 529; GSK1059615; ZSTK474; PWT33597; IC87114; TG100-115; CAL263; RP6503; PI-103; GNE-477; CUDC-907; AEZS-136 and those disclosed in U.S. Pat. No. 8,586,574; WO 2012/082997 and WO 2014/005182.

In particular embodiments, the PARP inhibitor is administered in combination with a PKCβ inhibitor, such as is Enzastaurin (LY317615), to sensitize the cancer to PARP inhibitor therapy. Other example of PKCβ inhibitors include Ro 31-8220, PKC-412, UCN-01, Gouml 6983, Hispidin, Bisindolylmaleimide I (GF 109203X), Bisindolylmaleimide I HCl, and LY-333,531 Hydrochloride.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the prevention or treatment of disease, the appropriate dosage of a therapeutic composition, e.g., a PARP inhibitor, will depend on the type of disease to be treated, as defined above, the severity and course of the disease, whether the agent is administered for preventive or therapeutic purposes, previous therapy, the patient's clinical history and response to the agent, and the discretion of the physician. The agent is suitably administered to the patient at one time or over a series of treatments.

B. Pharmaceutical Compositions

Also provided herein are pharmaceutical compositions and formulations comprising the PARP inhibitor, optionally an additional anti-cancer agent and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.).

A. Combination Treatments

The methods and compositions, including combination therapies, enhance the therapeutic or protective effect, and/or increase the therapeutic effect of another anti-cancer or anti-hyperproliferative therapy. The additional therapy may be radiation therapy, surgery (e.g., lumpectomy and a mastectomy), chemotherapy, targeted molecular inhibitor, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant, neoadjuvant, or palliative therapy.

Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a PARP inhibitor therapy is "A" and an anti-cancer therapy is "B":

| |
|---|
| A/B/A B/A/B B/B/A A/A/B A/B/B B/A/A A/B/B/B B/A/B/B |
| B/B/B/A B/B/B/A A/A/B/B A/B/A/B A/B/B/A B/B/A/A |
| B/A/B/A B/A/A/B A/A/A/B B/A/A/A A/B/A/A A/A/B/A |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium;

tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies that may be used include immune adjuvants, e.g., *Mycobacterium bovis*, *Plasmodium falciparum*, dinitrochlorobenzene, and aromatic compounds; cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, may be used. CT-011, also known as hBAT or hBAT-1, may be used. AMP-224, also known as B7-DCIg, is a PDL2-Fc fusion soluble receptor.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. Antibodies that compete with any of these art-recognized antibodies for binding to CTLA-4 also can be used. For example, a humanized CTLA-4 antibody is described in U.S. Pat. No. 8,017,114; incorporated herein by reference.

An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors and immunoadhesions. 4. Surgery Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. 5. Other Agents It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

Further embodiments of the present disclosure include kits for the measurement, analysis, and reporting of gene expression and transcriptional output. A kit may include, but is not limited to microarray, quantitative RT-PCR, or other genomic platform reagents and materials, as well as hardware and/or software for performing at least a portion of the methods described. For example, custom microarrays or analysis methods for existing microarrays are contemplated. Accordingly, an article of manufacture or a kit is provided comprising a customized assay for determining the gene signature score also provided herein. The article of manufacture or kit can further comprise a package insert comprising instructions for using the customized assay to determine the gene signature score and to then treat or delay progression of breast cancer or ovarian cancer in an individual. Probes for any of the genes described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Prediction of Drug Response and Synergizing Agents

Iterative resampling analysis to predict sensitivity (IRAPS) of cancer cell lines to therapeutic agents: As gene expression data has proven to have a robust capacity for predicting drug sensitivity (Costello et al., 2014), a pipeline was developed based on the stochastic sampling of gene expression data from publically available databases (Barretina et al., 2012). The iterative resampling analysis to predict sensitivity (IRAPS, FIG. 1A) algorithm used gene expression data from 857 solid tumor derived cancer cell lines from the Cancer Cell Line Encyclopedia (CCLE), matched with drug sensitivity data from the Genomics of Drug Sensitivity in Cancer (GDSC) (Yang et al., 2013). The reported sensitivity values were transformed into z-scores, defining "responders" defined as having z-scores of less than −1 and "non-responders" defined as having z-scores that were greater than 0. If multiple drugs were available for a given target, sensitivity values for both inhibitors were called and averaged after converting to z-scores. After 1000 iterations using the complete cell line set, the results were then transferred to a grid-search optimization algorithm for maximization of drug sensitivity prediction accuracy in the desired tumor type. This algorithm tested each threshold value for fold changes, p-values, and the fraction of times the gene was identified at each p-value/fold change threshold to determine which combination produced the optimal area under the curve (AUC) value for the receiver operator characteristic (ROC) curve, resulting in a final therapeutic target sensitivity.

Figure 1B:
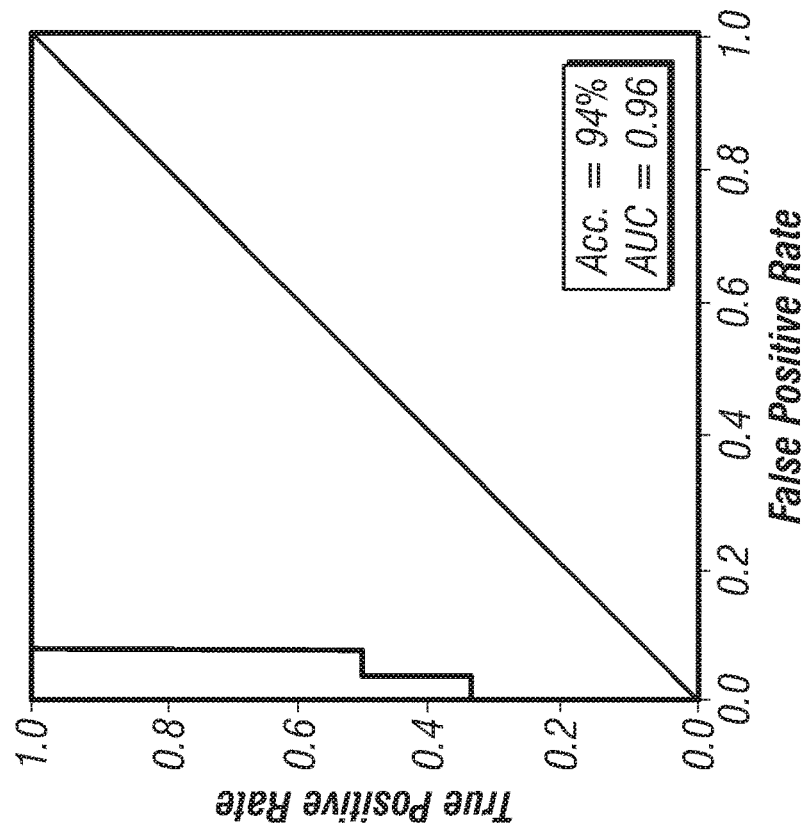
Figure 1C:
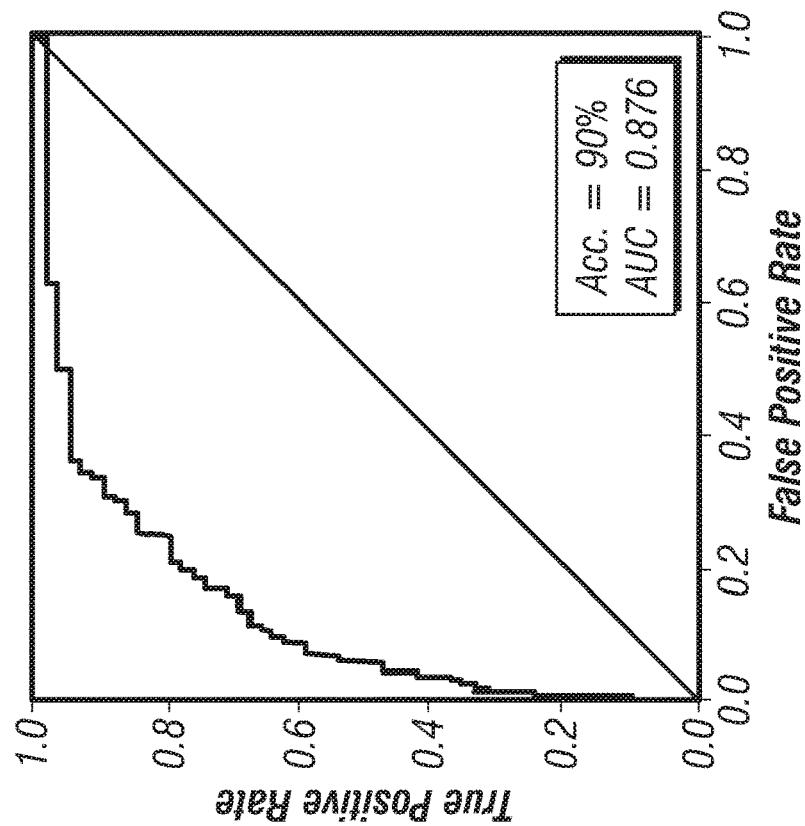
Figure 7:
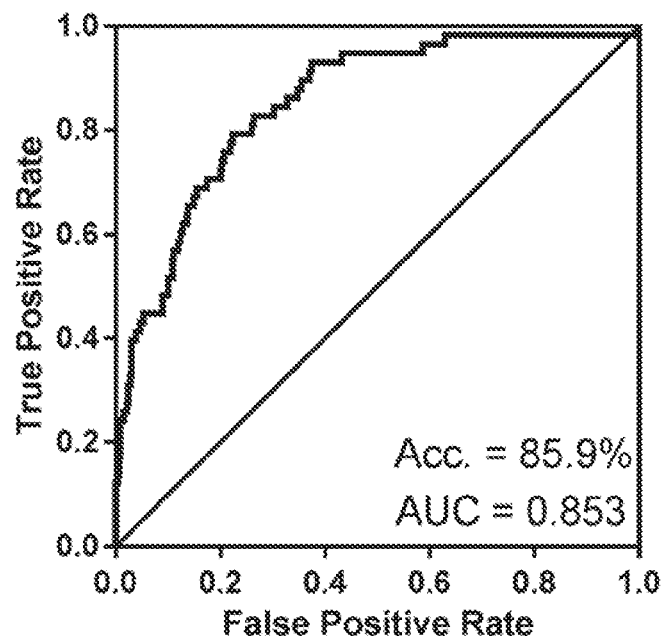
FIG. 7: The HER2 inhibitor signature predicts independent of ERBB2 and ERBB3 expression. After excluding ERBB2 and ERBB3 from the HER2 inhibitor sensitivity gene expression, results were re-calculated and showed minimum deviation from the full signature indicating these two genes are not largely responsible for the accuracy of the signature.

For an initial training test of this pipeline, it was sought to predict the sensitivity of breast cancer cells to dual HER2/EGFR inhibitors by using sensitivity data for neratinib and lapatinib. Optimization resulted in a 32 gene expression signature for HER2 inhibitor (HER2i, Table 3) sensitivity in breast cancer cell lines. The efficacy of this signature was confirmed in an independent testing set of cell lines treated with afatinib, yielding an AUC value of 0.96 with 94% accuracy (FIG. 1B). This signature identified ERBB3, which has been previously implicated in lapatinib response (O'Neill et al., 2012). To investigate if these cell line-derived signatures were relevant in patient cohorts, the signature was applied to TCGA breast cancer gene expression datasets (Lord and Ashworth, 2016) to test the ability to identify patients within the HER2/ERBB2 breast cancer subtype and would likely be sensitive to HER2i. Though a population of the HER2/ERBB2 subtype may harbor innate resistance to HER2 inhibitors, or a subset of other subtypes may show response, the large enrichment within the HER2/ERBB2 subtype suggests the accurate prediction of responders to HER2 inhibition within breast cancer patients. While this signature did include ERBB2 and ERBB3, manually excluding these genes did not significantly alter prediction accuracy (FIG. 7). This analysis showed that the signature could identify the patients within the HER2/ERBB2 subtype with 90% accuracy (FIG. 1C), indicating the IRAPS approach could identify clinically relevant gene expression signatures from cell line drug sensitivity data.

TABLE 3

HER2 inhibitor sensitivity gene signature.

| Gene | Fold Change |
| --- | --- |
| ERP27 | 2.81432 |
| EPCAM | 2.60499 |
| ESRP1 | 2.52034 |
| MAL2 | 2.48233 |
| TSPAN1 | 2.41504 |
| GALNT3 | 2.1823 |
| BLNK | 2.14847 |
| ITGB6 | 2.11554 |
| EPN3 | 2.09707 |
| FAM110C | 2.04333 |
| MPZL2 | 2.03463 |
| ERBB2 | 2.03079 |
| LSR | 2.01818 |
| SPINT2 | 1.9935 |
| ERBB3 | 1.98092 |
| GRB7 | 1.96671 |
| ST14 | 1.94497 |
| GPR110 | 1.88065 |
| CDS1 | 1.87376 |
| C1orf116 | 1.85505 |
| SPINT1 | 1.84503 |
| GRHL2 | 1.84403 |
| EFNA1 | 1.7752 |
| ESRP2 | 1.7523 |
| ZEB1 | −1.79164 |
| FAM216A | −1.82765 |
| CCDC88A | −1.84791 |
| LOC100506844 | −1.85215 |
| POSTN | −1.87303 |
| RBM24 | −1.92972 |
| TMEM158 | −2.18227 |
| EMP3 | −2.50306 |

IRAPS accurately predicts patient survival following cisplatin treatment: To test the ability of IRAPS to predict sensitivity for a chemotherapeutic with a less-well defined profile, a sensitivity signature was developed for cisplatin. In order to have a sufficient sample size to allow for independent training and test groups, the signature was optimized for both serous ovarian cancer cell lines and triple-negative breast cancer cell lines. These cancers share many molecular commonalities, suggesting that there may be similar therapeutic vulnerabilities (Koboldt et al., 2012). The resulting 26 multigene expression signature (Table 2) was highly predictive of cisplatin sensitivity in the test data set, yielding an AUC of 0.81 (FIG. 2A).

Figure 2C:
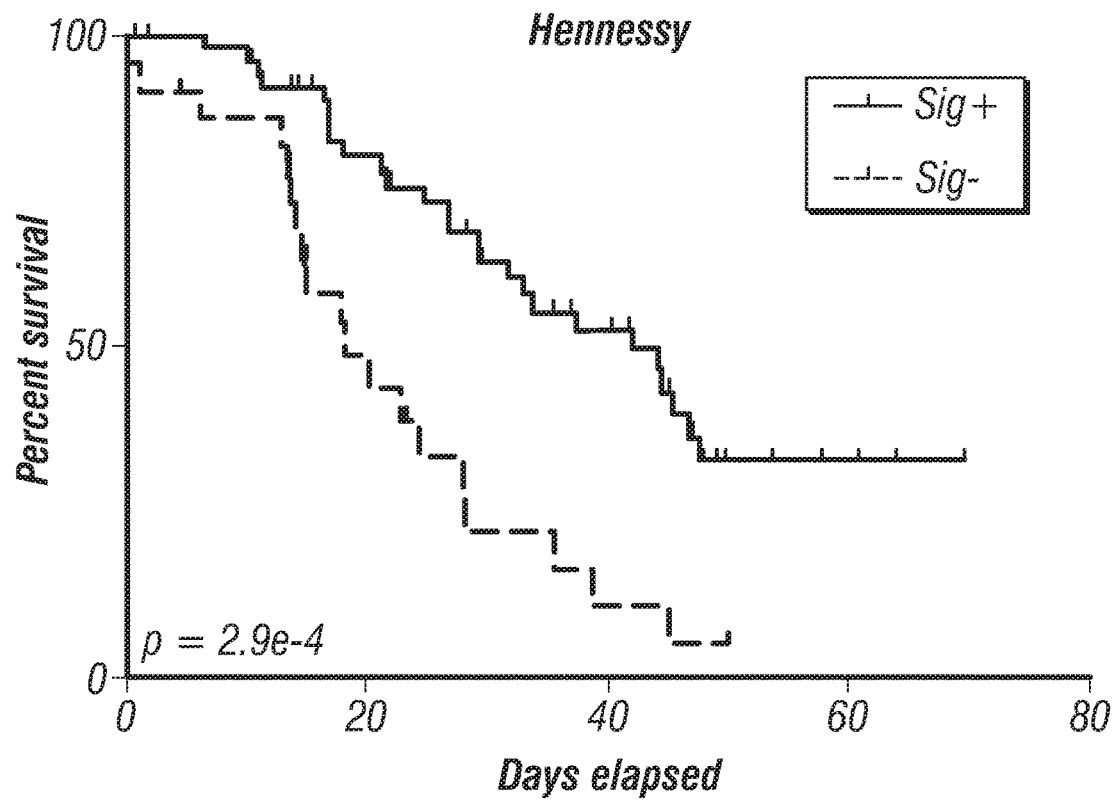
Figure 2D:
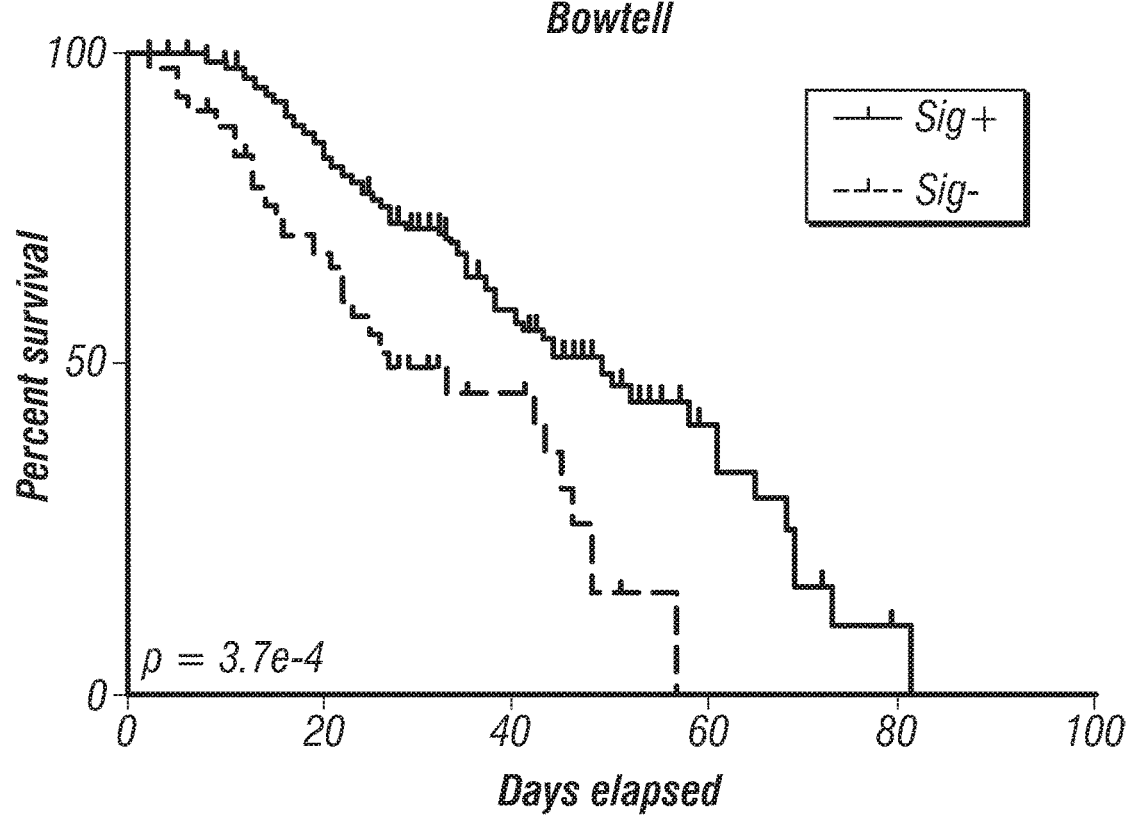
Figure 2E:
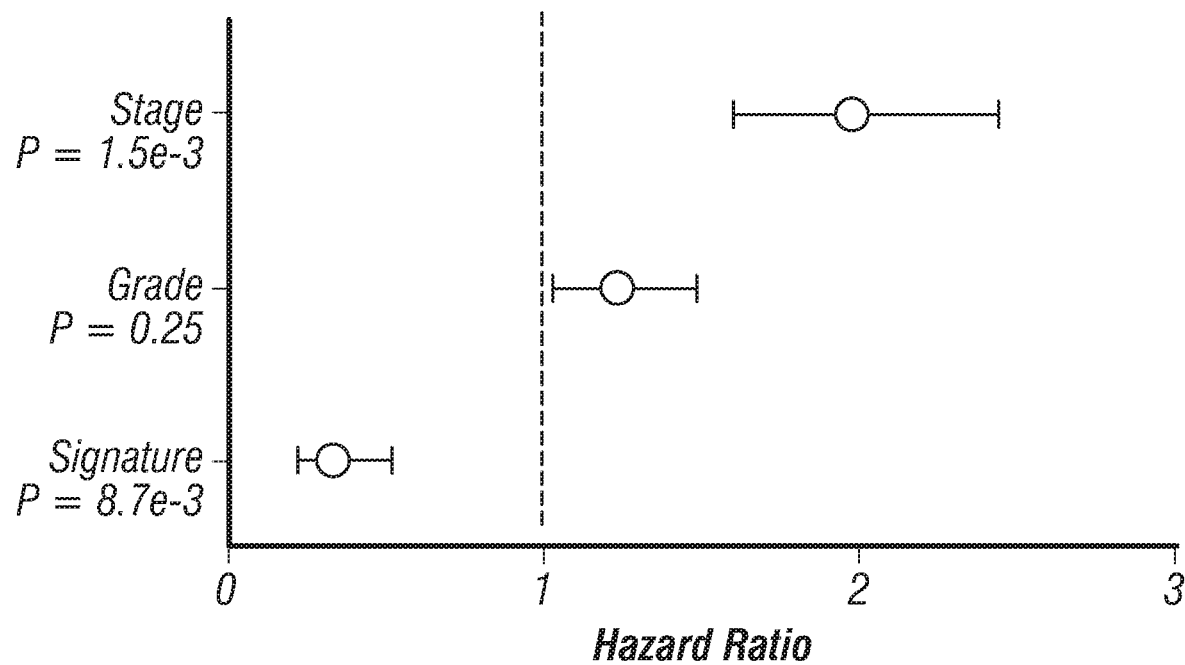
Figure 2F:
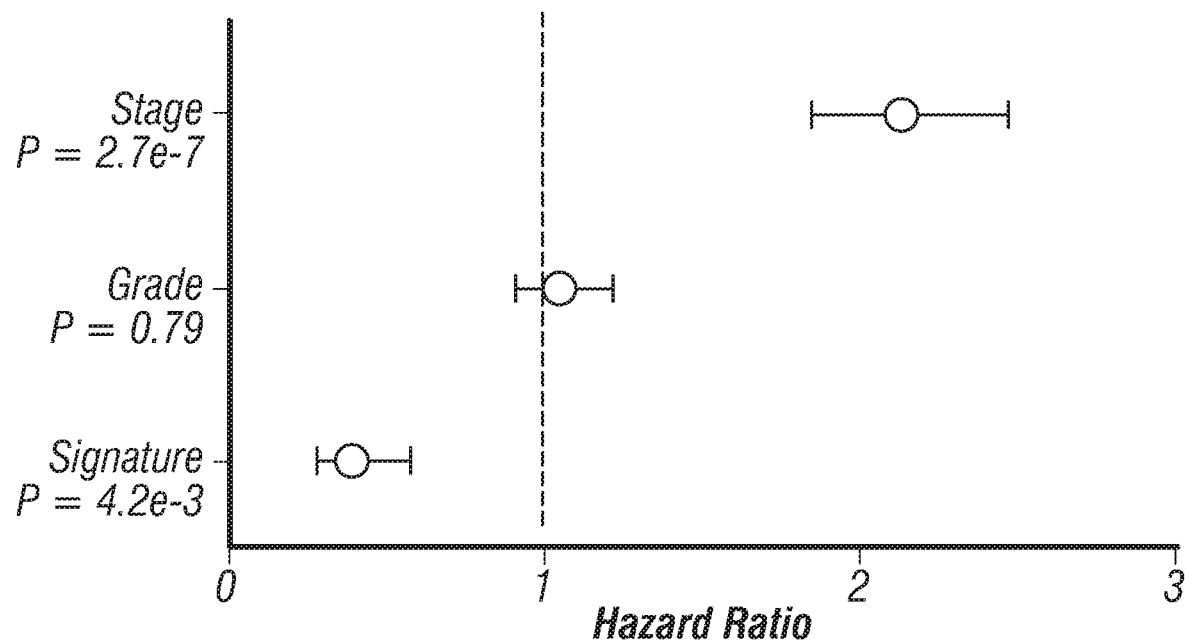
Figure 8:
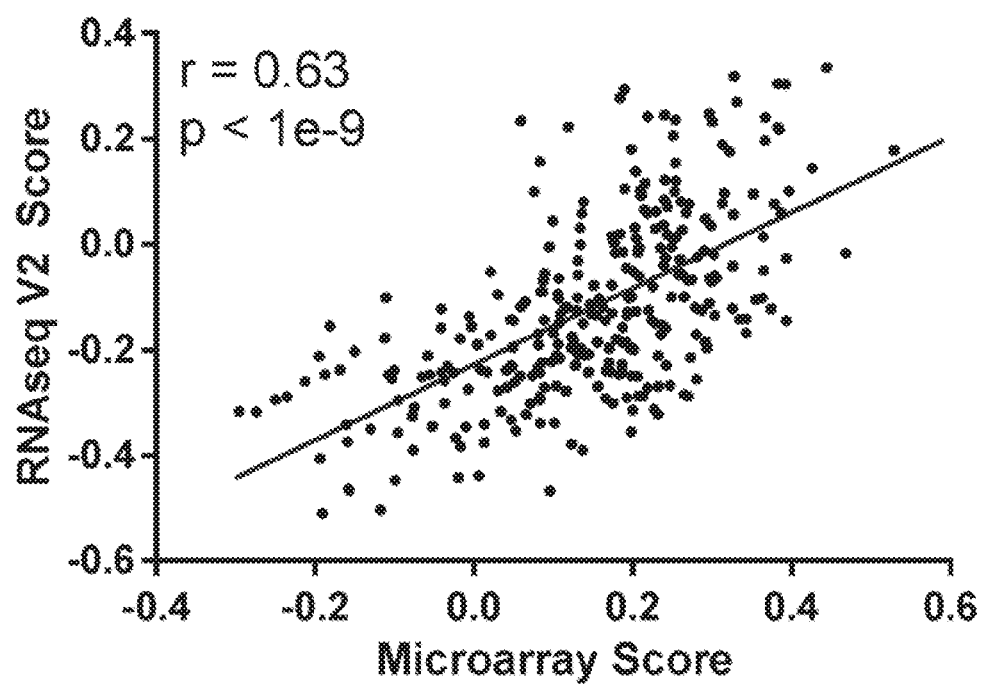
FIG. 8: Gene expression signature score is not dependent on profiling method. Cisplatin sensitivity scores were calculated for ovarian cancer patients from the TCGA that were transcriptionally profiled both by RNAseq V2 (Illumina HiSeq) and microarray (Affymetrix U133A). Both scores show strong correlation, indicating the approach is largely independent of profiling approach

Defects in the ability of cells to repair DNA double stranded breaks contributes significantly to cisplatin sensitivity as a result of HR defects that are typically present in BRCA-mutant tumors or other phenotypically similar BRCA-like tumors (Lord and Ashworth, 2016). Thus, to evaluate the predictive ability of the IRAPS generated signature, it was compared to an established clinically-derived BRCAness signature (Konstantinopoulos et al., 2010). This approach offered an improvement on BRCAness predictability, as evidenced by an increased ROC AUC (FIG. 2B). Next, to validate this signature in patient cohorts, two independent ovarian cancer patient cohorts that were treated with cisplatin were analyzed, with clinical-pathological characteristics of these cohorts are given in Table 2. It was found that the cisplatin sensitivity signature predicted patient survival in both cohorts (FIG. 2C-D). Since both of these cohorts had gene expression profiled by microarray, TCGA samples profiled by both RNAseq and microarray were used to determine if the signature was sensitive to the technique used to profile samples. A strong correlation was found between the score calculated through microarray and RNA sequencing suggesting the signature is rather insensitive to the profiling technique (FIG. 8). Moreover, the use of a Cox proportional hazards model suggested that this survival prediction was independent of both tumor stage and grade (FIG. 2E-2F). These results compare favorably with previous signatures of platinum sensitivity derived from patients, with the cell line-derived signature yielding a multivariate hazard ratio of 0.33 (0.22-0.51) compared to hazard ratios of 0.30 (0.11-0.83) and 0.59 (0.34-1.01) (Kang, D'Andrea, and Kozono, 2012). This suggests that the signature derivation method can equal the accuracy of patient-derived signatures, enabling personalization of new chemotherapeutics in absence of large cohorts of patient data.

TABLE 4

Clinical-pathological characteristics of cisplatin-treated cohorts.

|  | Total | Percent |
|---|---|---|
| Bowtell | | |
| Number of Patients | 243 | |
| Age | | |
| Median | 59 | |
| Range | 23-80 | |
| Grade | | |
| 1 | 9 | 3.7 |
| 2 | 89 | 36.6 |
| 3 | 144 | 59.3 |
| Unknown | 1 | 0.4 |
| Stage | | |
| I | 14 | 5.8 |
| II | 12 | 4.9 |
| III | 195 | 80.2 |
| IV | 21 | 8.6 |
| Unknown | 1 | 0.4 |
| Subtype | | |
| Serous | 226 | 93.0 |
| Endometriod | 16 | 6.6 |
| Adenocarcinoma | 1 | 0.4 |
| Hennessy | | |
| Number of Patients | 87 | |
| Age | | |
| Median | 60.8 | |
| Range | 37.3-88.4 | |

TABLE 4-continued

Clinical-pathological characteristics of cisplatin-treated cohorts.

|  | Total | Percent |
|---|---|---|
| Grade | | |
| 1 | 7 | 8.0 |
| 2 | 16 | 18.4 |
| 3 | 61 | 70.1 |
| Unknown | 3 | 3.4 |
| Stage | | |
| I | 5 | 5.7 |
| II | 11 | 12.6 |
| III | 58 | 66.7 |
| IV | 11 | 12.6 |
| Unknown | 2 | 2.3 |
| Subtype | | |
| Serous | 80 | 92.0 |
| Endometriod | 1 | 1.1 |
| Clear cell | 1 | 1.1 |
| Mucinous | 1 | 1.1 |
| Mixed | 2 | 2.3 |
| Unknown | 2 | 2.3 |

Figure 2G:
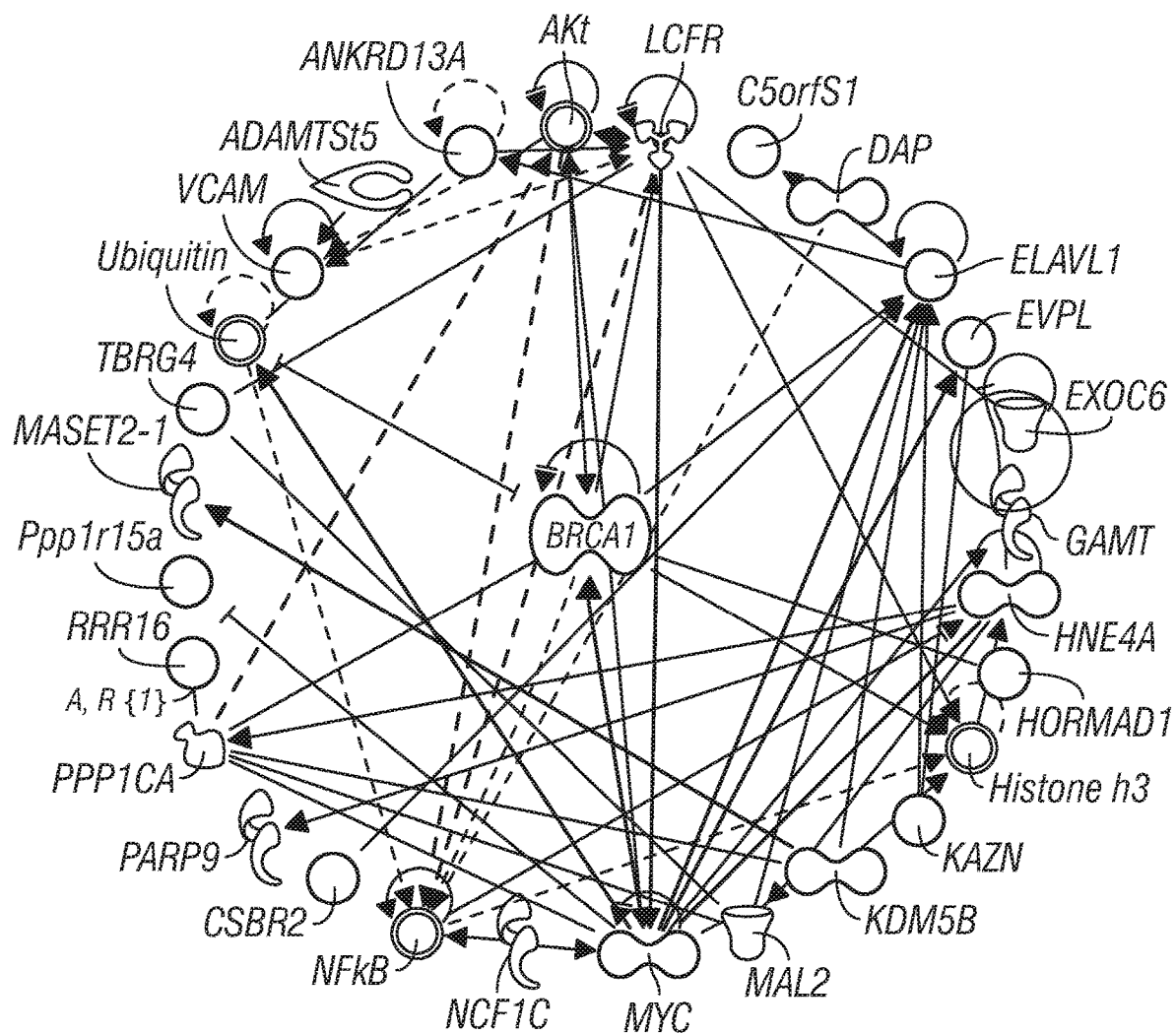

To understand what molecular changes the cisplatin sensitivity signature was detecting, Ingenuity Pathway Analysis was used and it was found that this signature predicted decrease in BRCA1 function, which may contribute to its predictive power (FIG. 2G). However, BRCA1 alone was not sufficient to predict responsive patients, as is evidenced by the low true positive rates in the BRCAness signature (FIG. 2B). Additional genes identified in the IRAPS signature, including the overexpression of DUSP6 (Li and Melton, 2012), and low level ERCC1 gene expression (Olaussen et al., 2006), have been previously identified as indicators of cisplatin sensitivity, and may therefore contribute to the accuracy of the signature.

Figure 3A:
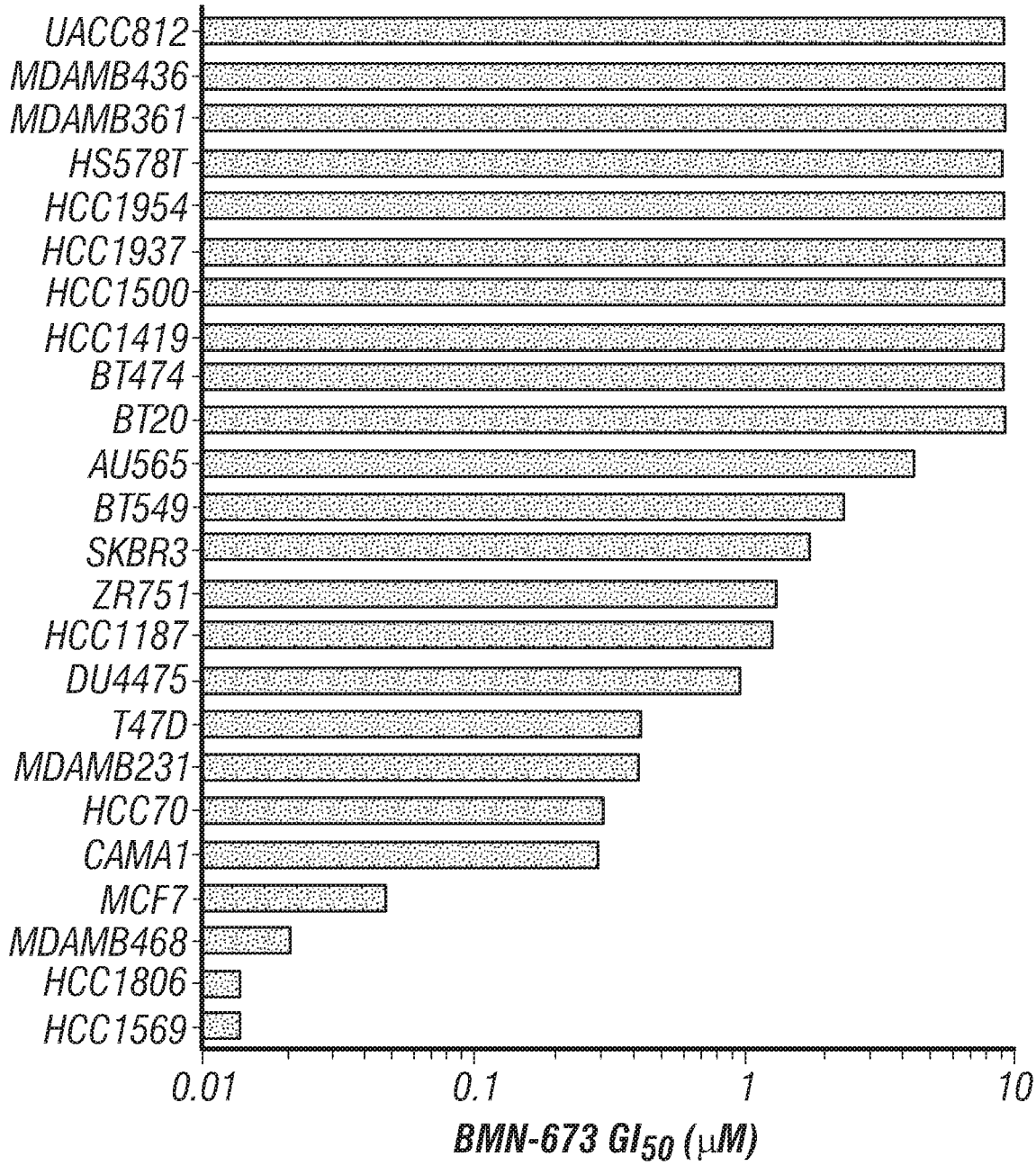
FIGS. 3A-3J: PARP sensitivity signature predicts response to PARP inhibitors in cell lines, patient-derived tumor cells (PDTCs), and patient-derived xenografts (PDXs).
Figure 3B:
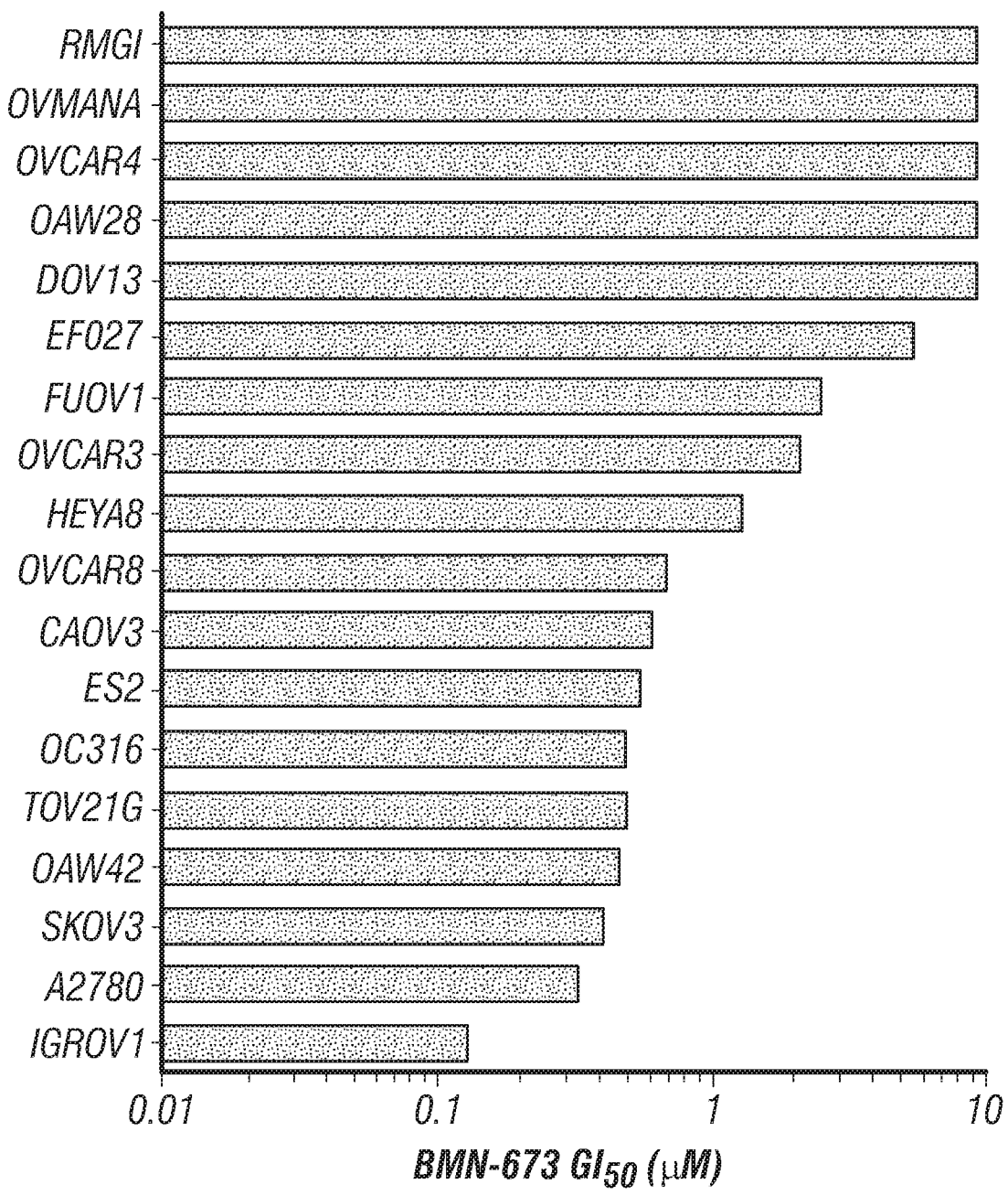
Figure 3C:
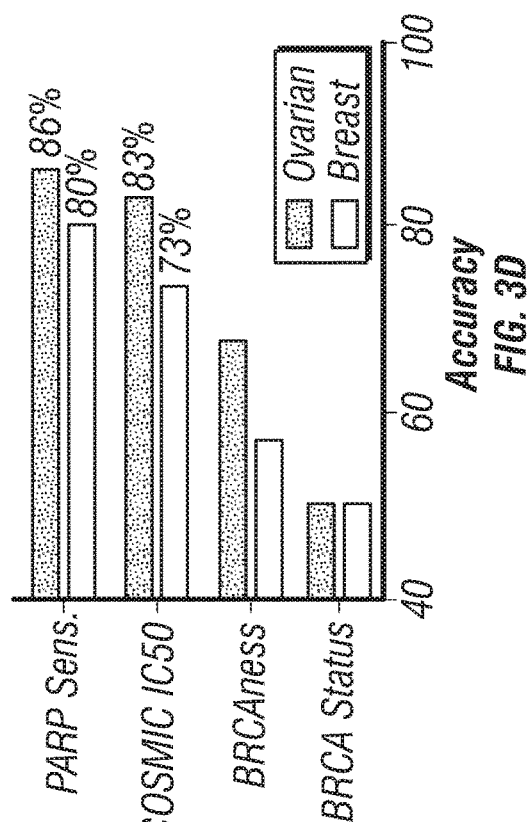
Figure 3D:
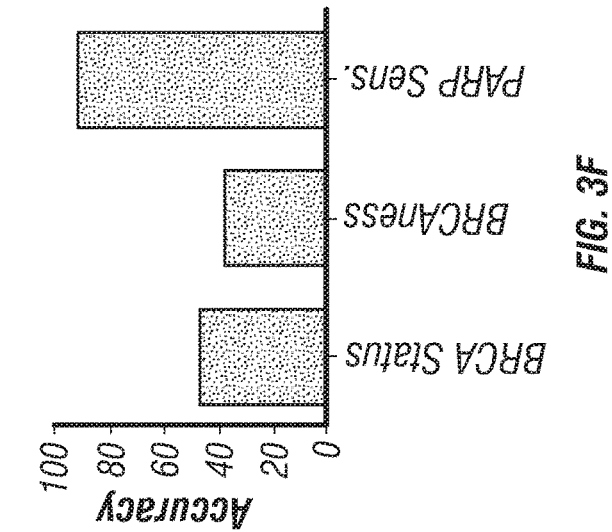

A PARP sensitivity signature improves identification of PARP-responsive tumors: PARP inhibitors have recently shown promise for the treatment of BRCA-mutant ovarian and breast cancers. However, it is unclear whether other patient populations may benefit from PARP inhibitors, as well as why the majority of BRCA-mutant patient tumors fail to respond to PARP inhibition. It was tested if a gene expression signature generated by IRAPS could improve patient selection for PARP inhibitors. For this analysis, the algorithm was again optimized for both ovarian and breast cancer cell lines by using sensitivity data for the PARP inhibitors AZD2281 (olaparib) and AG014699 (rucaparib) shown in Table 1. To generate an independent test set, a panel of breast and ovarian cancer cell lines were screened for sensitivity to the PARP inhibitor BMN-673 (FIG. 3A-B). Testing cell lines were excluded from the IRAPS pipeline. To determine an upper bound for signature accuracy, the PARPi sensitivity values from COSMIC were used to predict sensitivity in overlapping cell lines that were screened against BMN-673, and it was found that the gene signature performed equally well or better than this theoretical maximum attainable accuracy (FIG. 3C-D). To compare to more clinically relevant predictors, the signature's accuracy was compared to either using the clinically-derived BRCAness gene signature (Konstantinopoulos et al., 2010) as well as BRCA1/2 mutation status and found the current signature significantly outperformed both parameters (FIG. 3C-D). Of the evaluated breast cancer cell lines with mutations in BRCA1 (MDA-MB-436 and HCC-1937) or BRCA2 (HCC-1569, BT-20, BT-474, MDA-MB-361), only one (HCC- 1569) was found to respond to BMN-673. Not only was this predicted by the signature, but of the remaining 5 non-responding cell lines 4 were correctly identified as resistant, only misclassifying MDA-MB-436. Additional testing of MDA-MB-436 response for olaparib (AZD2281) demonstrated sensitivity to this second agent, indicating this could be a drug-specific mechanism of resistance.

Figure 3E:
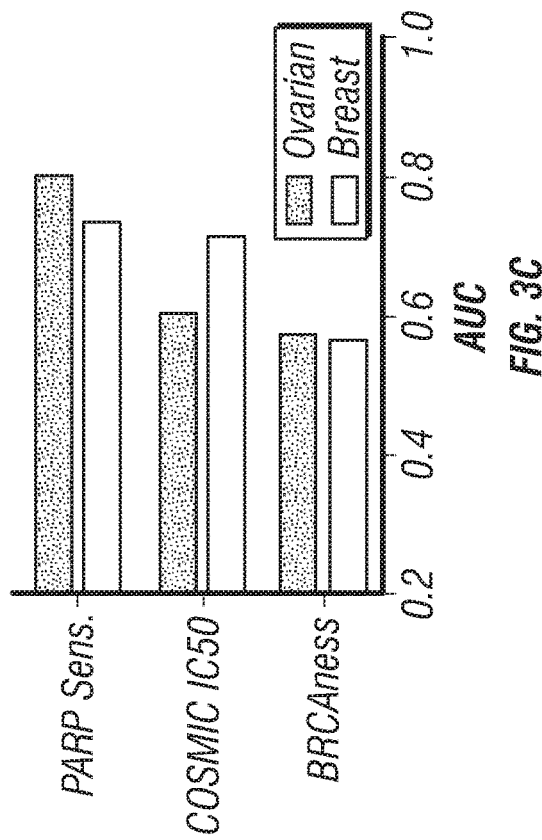
Figure 3F:
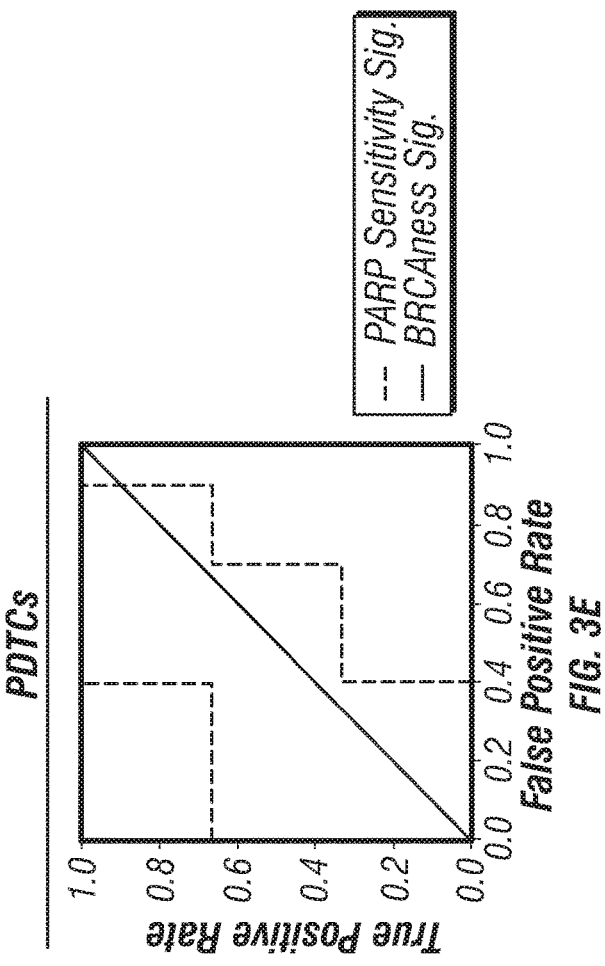
Figures 3G, 3H:
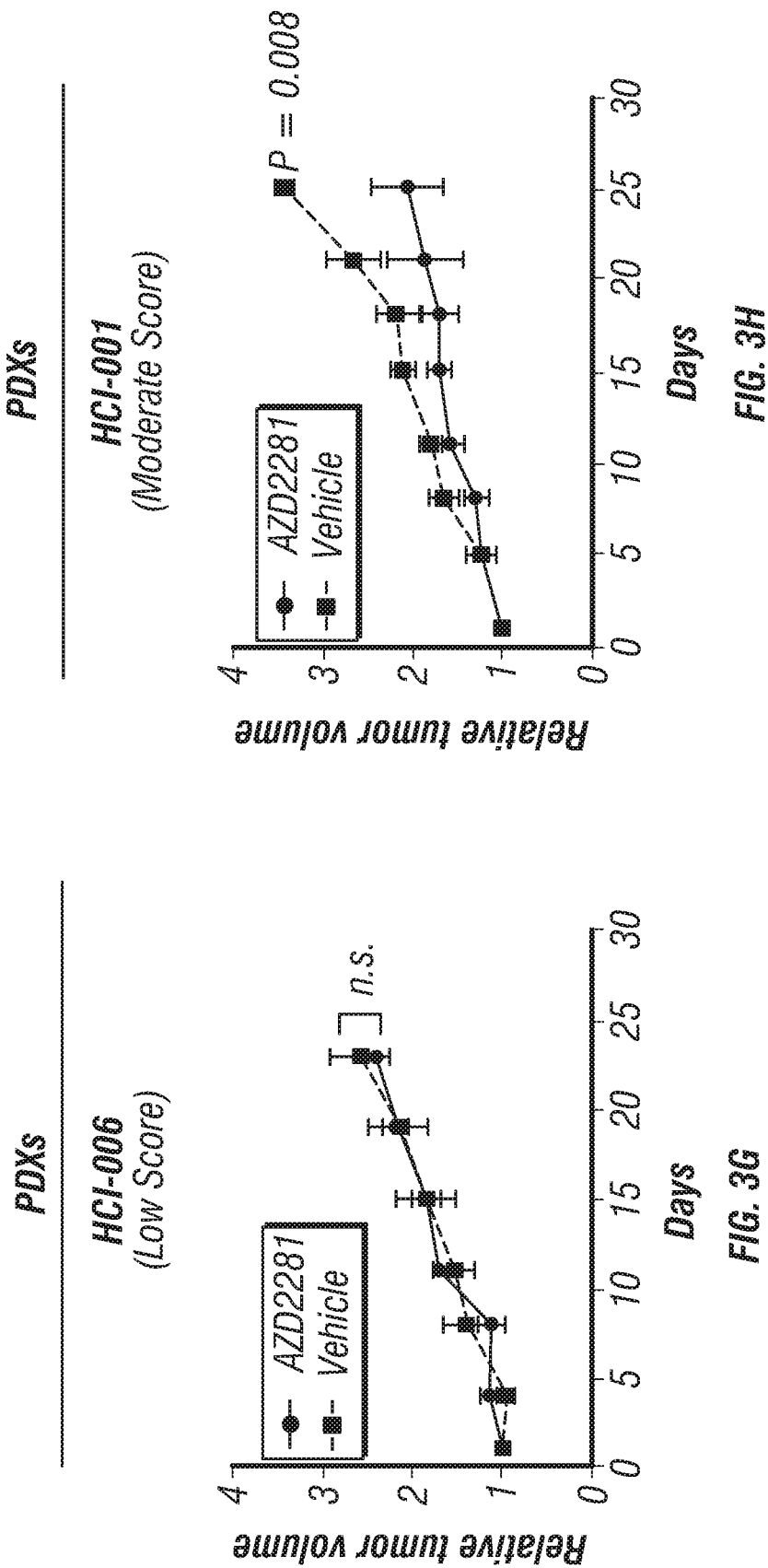
Figures 3I, 3J:
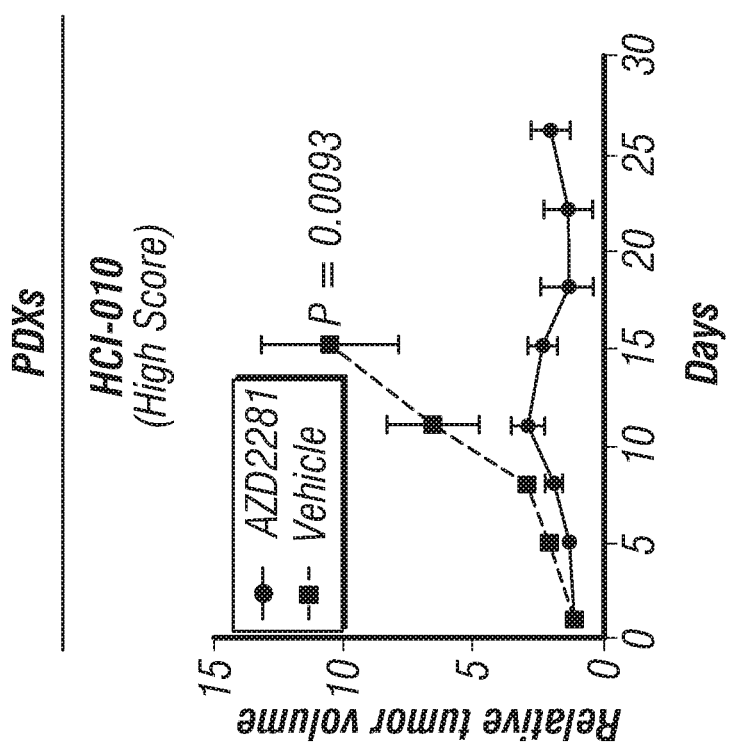

Next, the ability of the signature was investigated to predict response of a panel of primary patient-derived tumor cells to BMN-673 (Bruna et al., 2016). The PARPi sensitivity signature again outperformed BRCAness signature as shown by the ROC curve (FIG. 3E), as well as accuracy relative to BRCA1/2 mutation status (FIG. 3F). Notably, as observed with the breast cancer cell lines, the PARPi sensitivity signature accurately predicted the response of the two PARP-resistant BRCA1/2 mutants that had gained additional mutations (STG316 with mutant TP53BP1 and VHI0179 with mutant REV7) reversing their homologous recombination defective phenotype. Finally, to test the accuracy of the signature to predict in vivo responses, the response of 3 breast cancer PDX models were tested with varying PARPi sensitivity scores (FIG. 3G-I). As expected, the low scoring PDX, HCI-006, did not respond to the PARP inhibitor AZD2281, whereas the moderate scoring PDX, HCI-001, gave a partial response, and the highest scoring PDX, HCI-010, having near complete tumor growth inhibition (FIG. 3I). Correlation of AZD2281 treated versus control tumor volumes at day 15 displayed a strong negative correlation with the PARPi sensitivity score (FIG. 3J). This suggested that the PARPi sensitivity signature is capable of accurately predicting in vitro cell line responses and in vivo PDX responses to PARP inhibition. Taken together, these results demonstrate that the PARPi sensitivity signature can accurately identify tumors responsive to PARP inhibition both in BRCA1/2-mutant cohorts as well as broad panels of tumors.

Figure 4A:
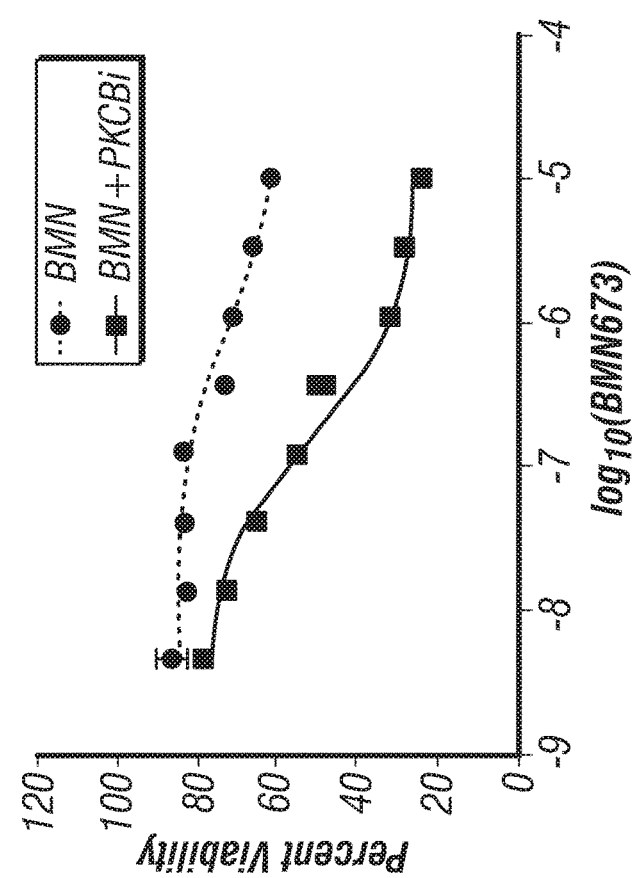
FIGS. 4A-4G: Identification of the PKCβ inhibitor Enzastaurin/LY317615 as a PARPi synergizing agent in breast and ovarian cancer cells.
Figure 4B:
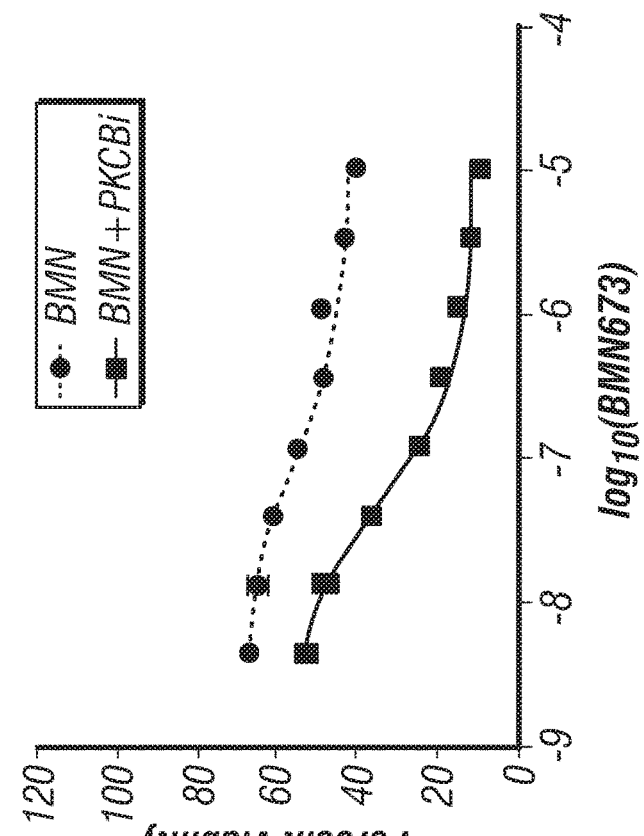
Figure 4D:
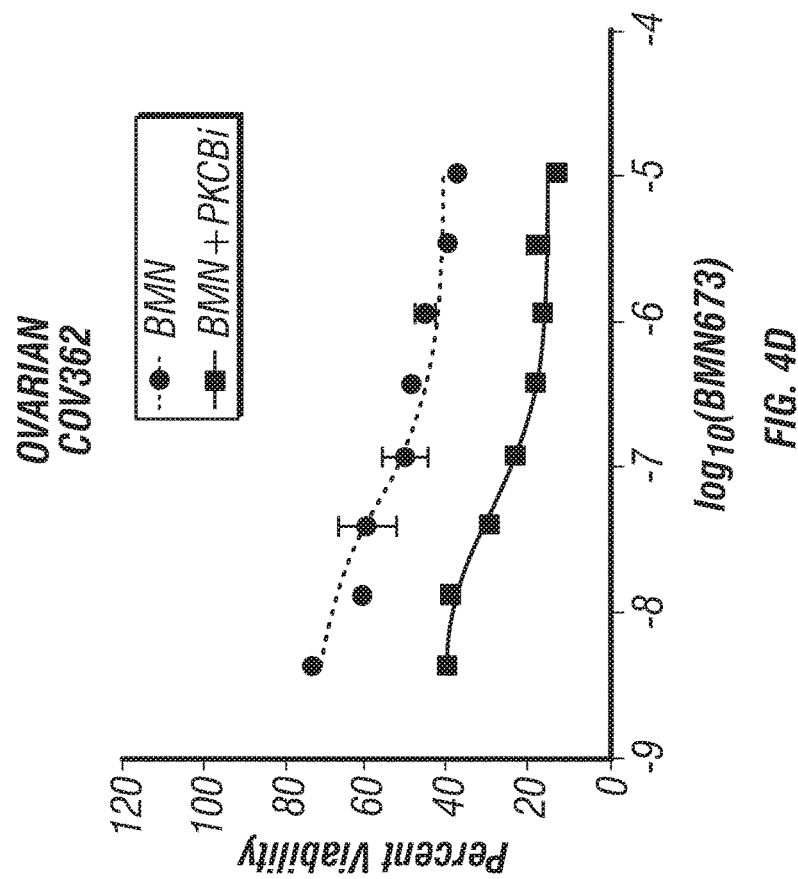
Figure 4C:
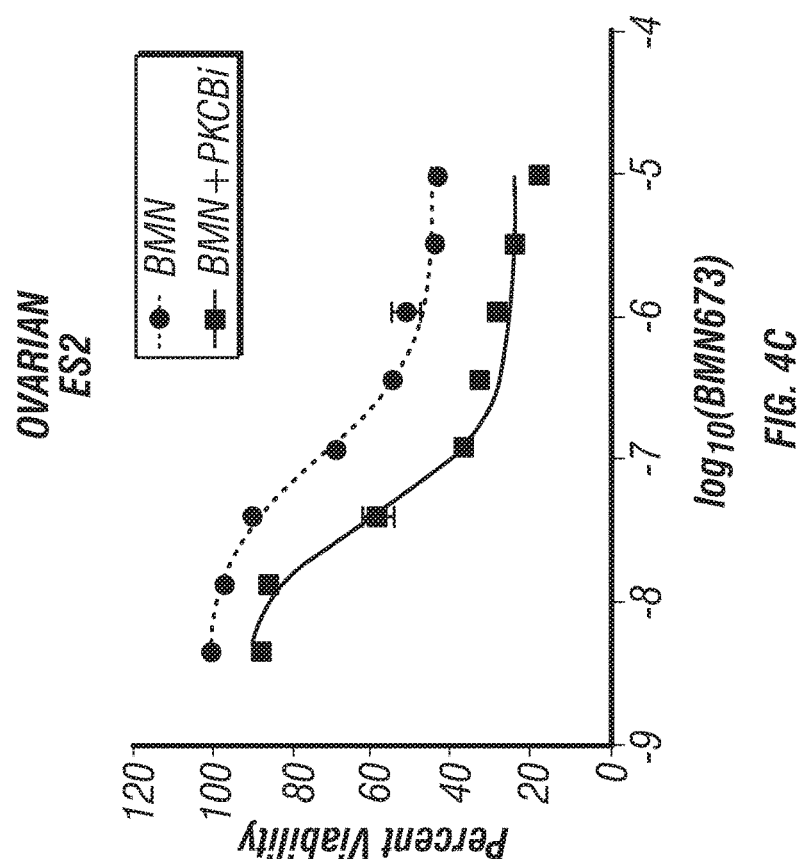
Figure 4F:
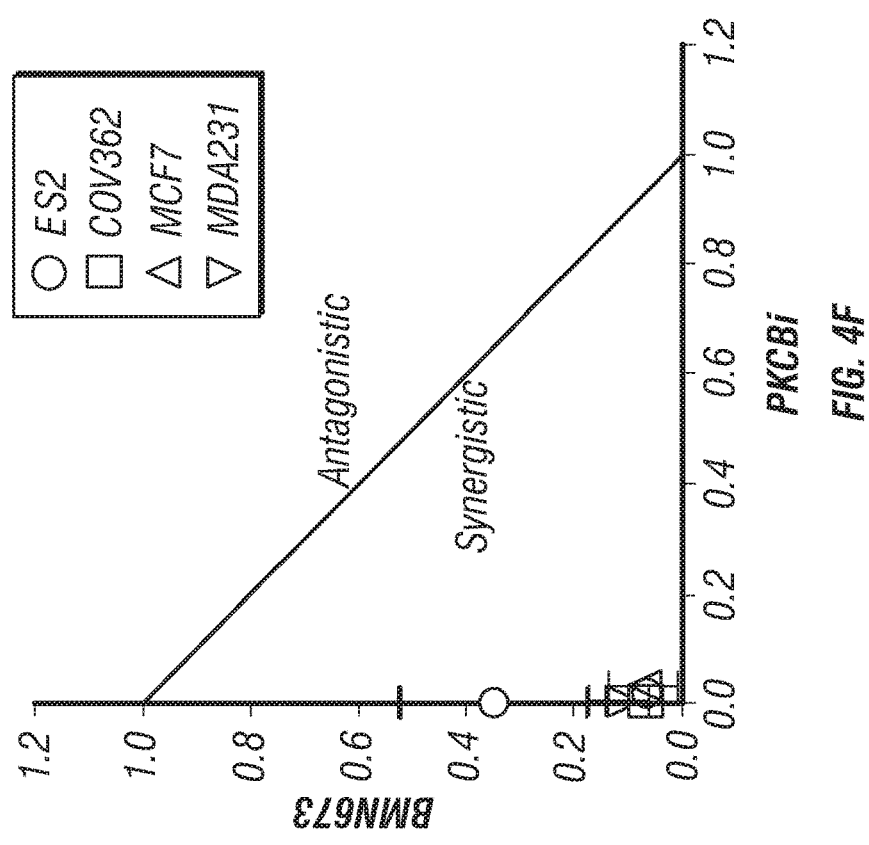
Figure 4E:
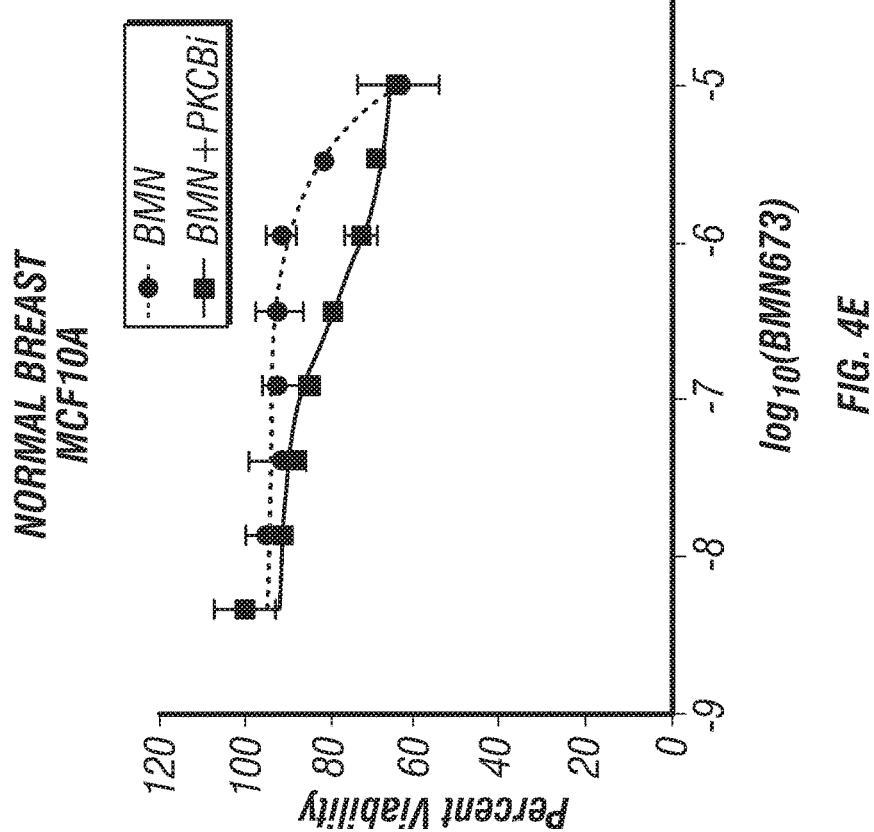
Figure 4G:
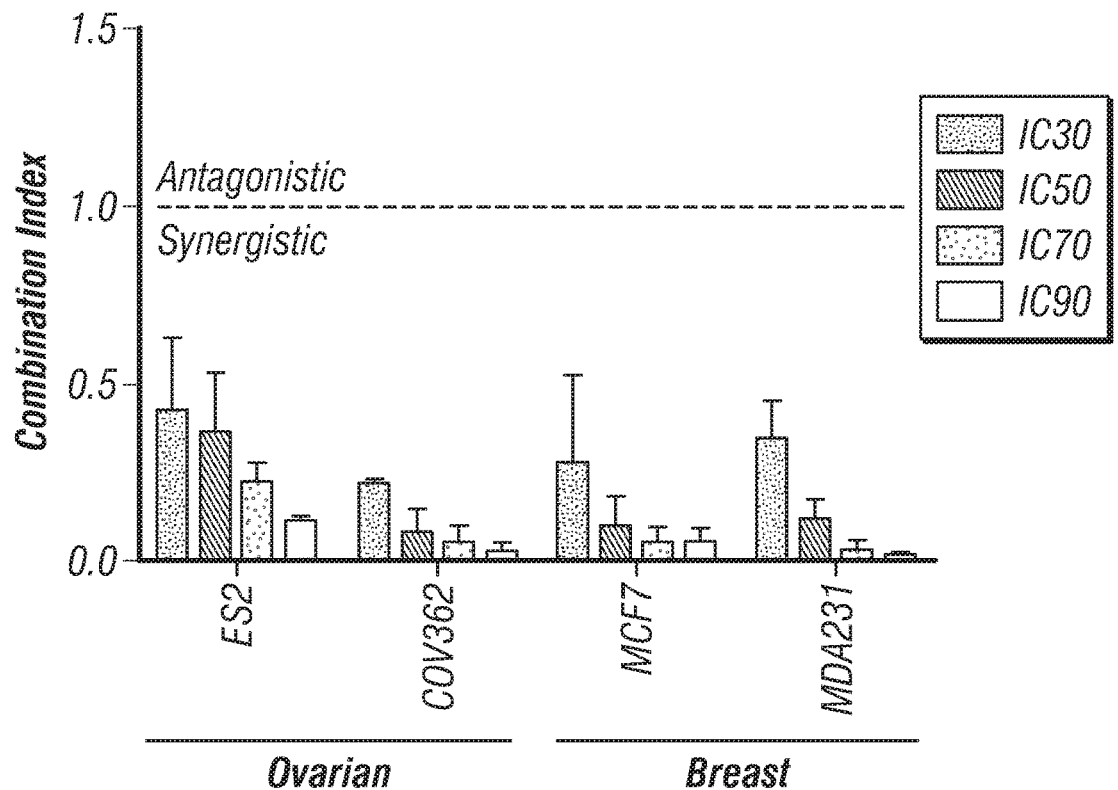
Figure 9:
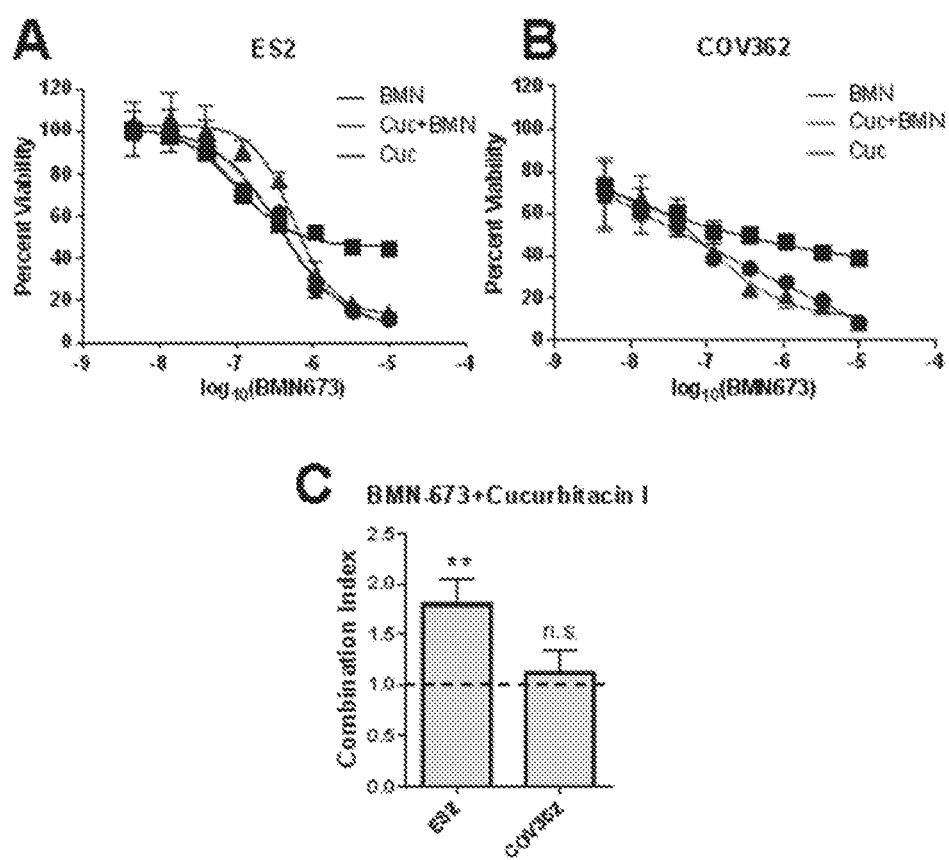
FIGS. 9A-9C: Drugs predicted to reverse PARPi sensitivity signature are antagonistic.

PARP sensitivity signature identifies PKCβ inhibitor Enzastaurin as a novel PARPi synergizing agent: Despite the promise of PARP inhibitor efficacy for the treatment of BRCA-mutated germline tumors, or in tumors that have a BRCAness phenotype, clinical trial objective response rates rarely exceed 50%. Thus, a clinical need remains for the improvement of methods to enhance PARP inhibitor efficacy. It was hypothesized that if the PARPi sensitivity signature could be induced through pharmacological intervention, combinatorial therapy with PARP inhibitors may improve on PARPi efficacy. Therefore, the PARPi signature was analyzed using a pipeline developed by the Library of Integrated Network-based Cellular Signatures (LINCS) program termed "lincscloud" (Broad.lincscloud). This program collects gene expression data following numerous chemical and genetic perturbations, allowing for the identification of possible inducers of the PARPi sensitivity signature. A top hit amongst molecules that were involved in clinical testing was an inhibitor of PKCβ. Initial testing of PKCβ inhibition in combination with the PARP inhibitor BMN673, revealed an enhanced PARP inhibitor response for both the triple negative breast cancer cell line MDA-MB-231 (FIG. 4A), and the luminal breast cancer cell line MCF7 (FIG. 4B). Not only did PKCβ inhibition synergize with PARP inhibition in breast cancer cell lines, the combinatorial efficacy was also evidenced for the BRCA wildtype ES2 (FIG. 4C) and BRCA-mutant COV362 ovarian cancer cell lines (FIG. 4D). This sensitization was greatly diminished in the non-tumorigenic MCF10A human mammary epithelial cell line (FIG. 4E). Isobolograms determined from $IC_{50}$ values indicate that PARP and PKCβ inhibition synergized in all tumorigenic cell lines (FIG. 4F). Moreover, quantification of synergism using the Chou-Talalay combination index method, where values that were less than 1 represented synergistic combinatorial therapies (Chou, 2006), demonstrated that this combination was synergistic in all evaluated cell lines across a wide range of concentrations (FIG. 4G). As this combination induced synergy in both BRCA-mutant and wild type cell lines with no dependency on basal sensitivity, this combination may be a viable treatment option to enhance efficacy in BRCA-mutant patients or cohorts predicted by the PARPi sensitivity signature. Conversely, it was found that Cucurbitacin I was predicted to reverse the PARPi sensitivity signature and thus tested to see if it would be antagonistic with PARP inhibitors (FIG. 9). As expected, this combination was found to be antagonistic in ES2 cells with less significant interaction between the drugs in COV362 cells, possibly because their BRCA mutation is too strongly sensitizing to PARP inhibitors to be reversed by chemical modulation.

Figure 5A:
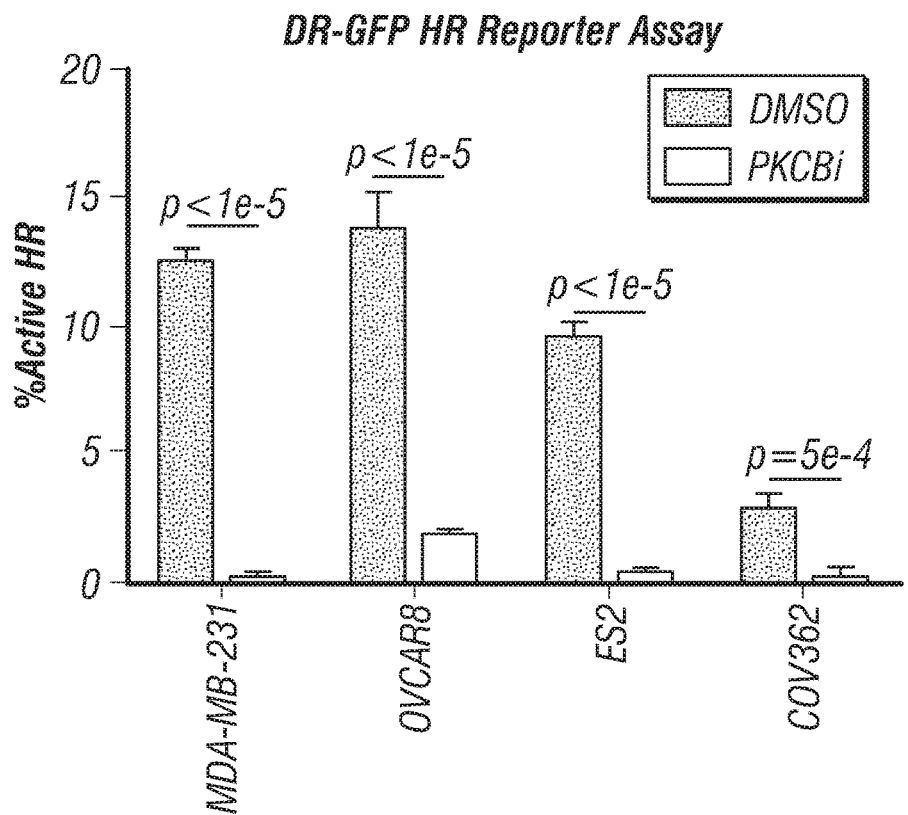
FIGS. 5A-5C: PKCβ inhibition induces deficiencies in homologous recombination.
Figure 5B:
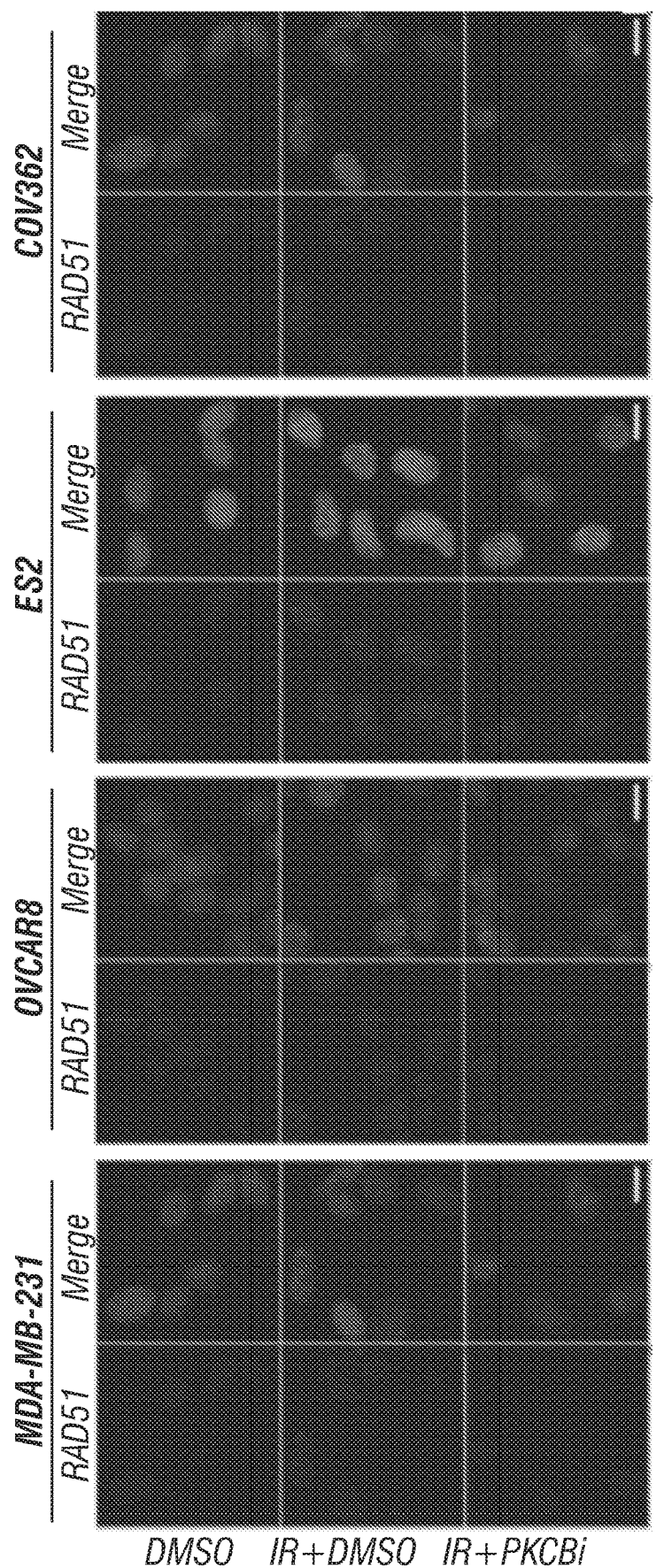
Figure 5C:
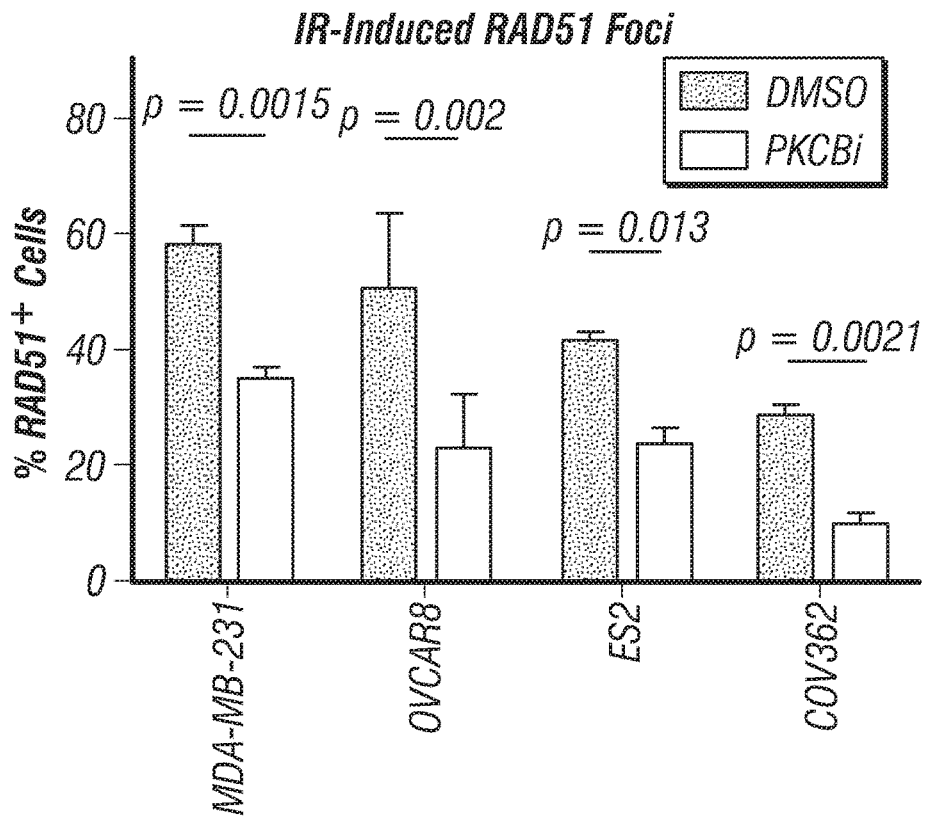
Figure 10:
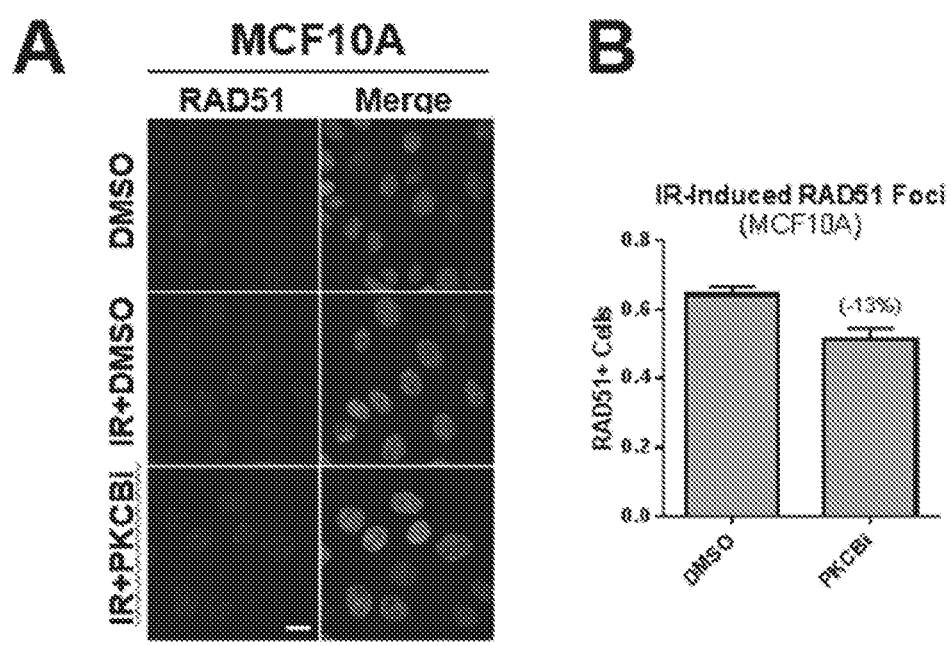
FIGS. 10A-10B: Minimal suppression of HR as indicated by RAD51 foci in non-malignant MCF10A cells.

Since PARP inhibitors should preferentially target cells with defective homologous recombination, it was hypothesized that PKCβ blockade was impairing HR. To test this, the DR-GFP reporter assay was used in which cells with a functional homologous recombination machinery will recombine the plasmid and express the GFP protein that is detectable by flow cytometry. As expected, the BRCA-mutant COV362 cell line had the lowest latent levels of homologous recombination. However regardless of the cell lines tested, homologous recombination activity was nearly completely abrogated with PKCβ inhibition (FIG. 5A). This result was tested by testing the ability of these cells to form RAD51 foci following irradiation, and found that RAD51 foci induction was reduced by over 50% (FIG. 5B-C). Comparing effects on the DR-GFP reporter assay relative to RAD51 foci formation as an indication of the extent of homologous recombination blockade suggested that PKCβ plays a role in the formation of RAD51 foci and in the later stages of homologous recombination. Moreover, this inhibition of HR was markedly reduced in non-tumorigenic MCF10A (FIG. 10). Taken together, not only was the IRAPS pipeline capable of generating a robust signature that accurately predicted PARPi sensitivity, but this resulting signature was also capable of predicting clinically relevant molecules that block HR and synergize with PARP inhibitors.

Figure 6A:
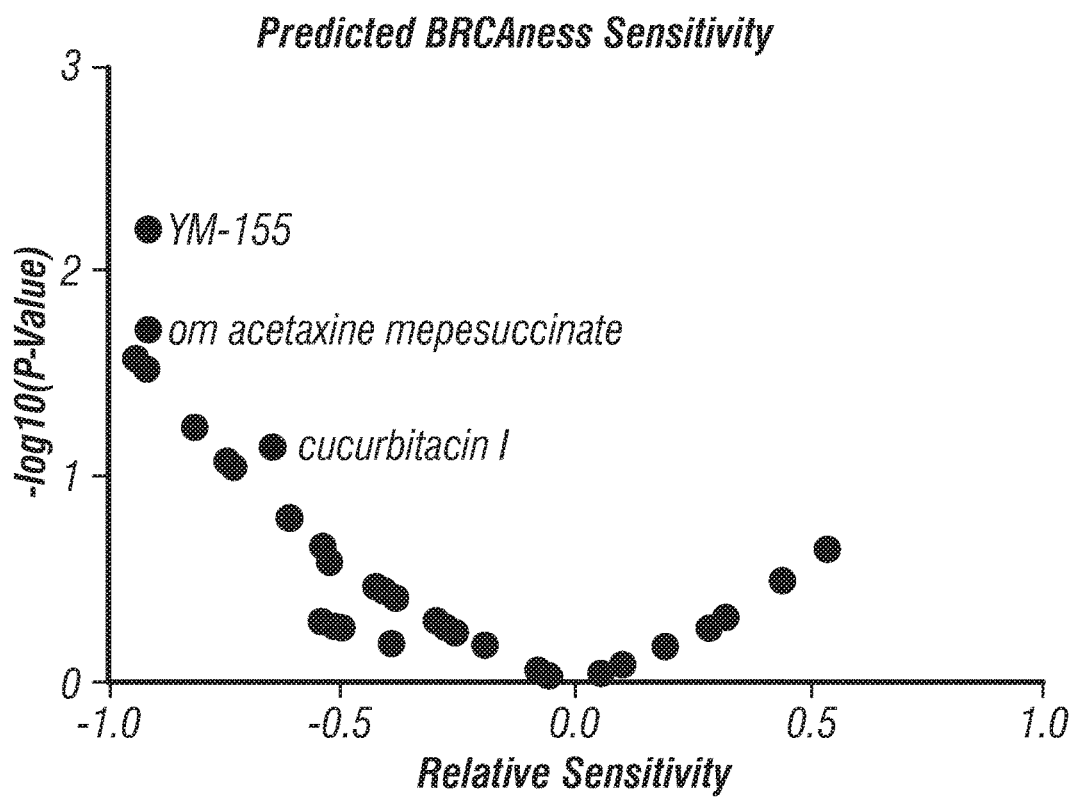
FIGS. 6A-6C: Use of the BRCAness signature to predict for targeted therapies reveals that the survivin inhibitor YM-155 specifically targets BRCA-like cells.
Figure 6B:
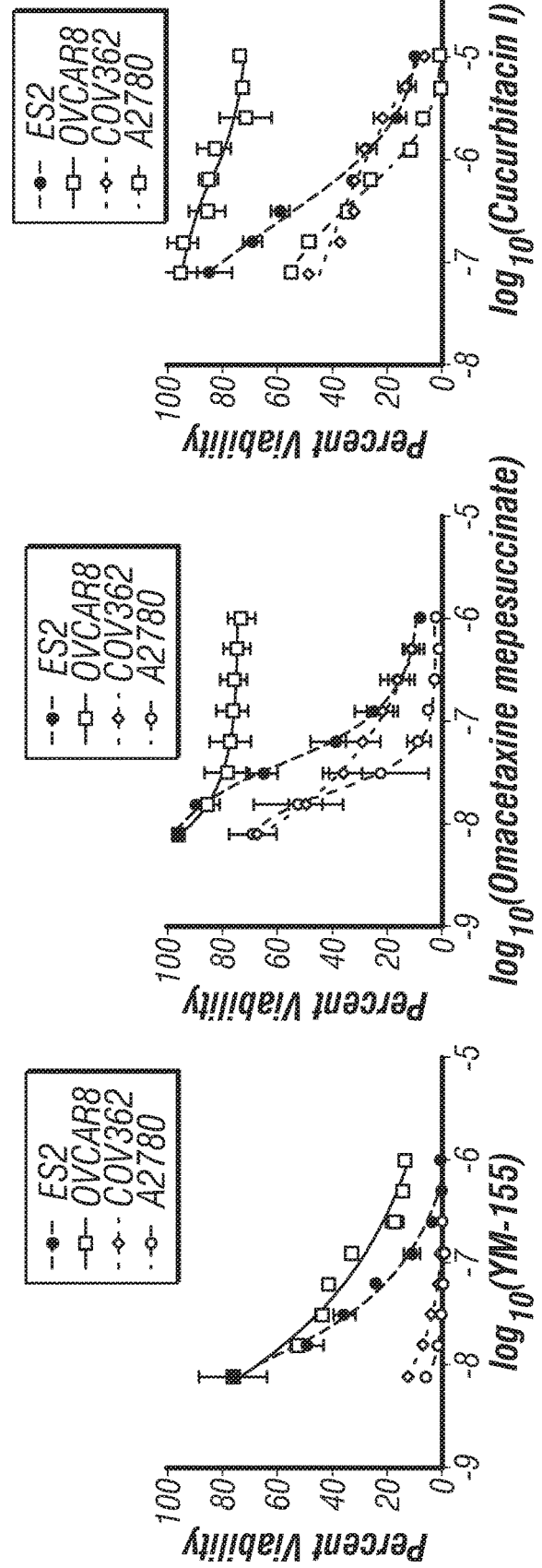
Figure 6C:
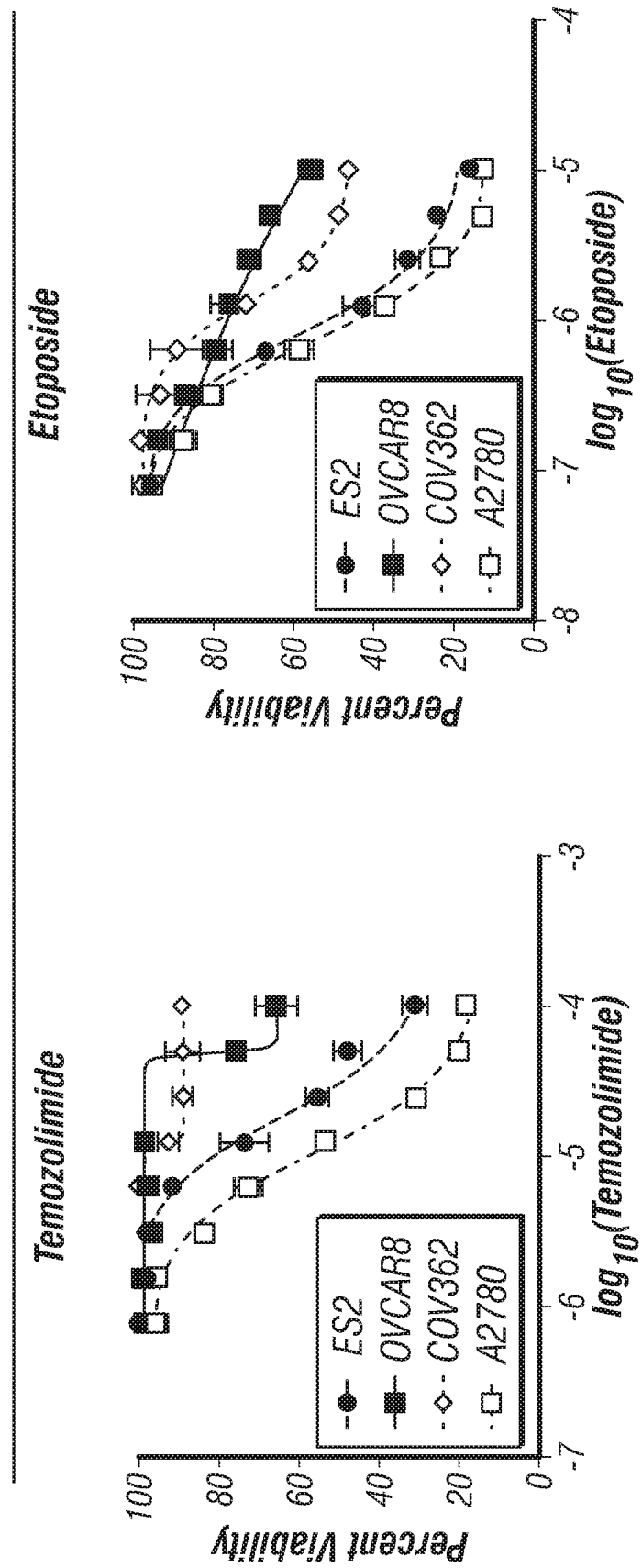

Prediction of BRCAness-targeting Drugs: Since the BRCAness signature was not predictive for either cisplatin or PARP inhibitors, it was questioned what drugs may potentially target BRCA-like cell lines. To investigate this, instead of classification based on drug sensitivity to ascertain differentially regulated genes, the BRCAness signature was applied to assign a BRCAness phenotype to cell lines, and then the CTRPv2 database was used to predict differential drug sensitivity. After excluding drugs with area under the response curve values of larger than 10, which is indicative of a general lack of cytotoxicity, three compounds were selected for further testing (FIG. 6A). These compounds were screened in four cell lines that were excluded from the initial analysis: BRCA mutant COV362 cells, BRCA-like CAOV4 cells, non-BRCA-like ES2 cells, and non-BRCA-like OVCAR8 cells. All three of the predicted BRCAness targeting drugs showed preferential toxicity in the BRCA-like cells (FIG. 6B). As expected, drugs that BRCA-like cells were predicted to be resistant to displayed diminished efficacies (FIG. 6C). While all predicted drugs showed some preferential inhibition of cells with a high BRCAness score, the survivin inhibitor YM-155 exquisitely targeted BRCA-like cells at nanomolar $IC_{50}$ amounts. Combination of YM-155 with the standard of care chemotherapeutics, cisplatin and paclitaxel, in BRCA-like ovarian cancer may be a promising treatment approach since early clinical trials in advanced non-small cell lung cancer have shown a favorable safety profile for YM-155 when combined with cisplatin and paclitaxel.

To further validate the PARP inhibitor gene signature, an in vivo study was performed in mice. Primary mammary gland tumors were dissected from 12-24 month old multiparous MMTV-LPAR1, LPAR2, LPAR3 or ENPP2 transgenic mice, carefully cleared of all stromal/fat and necrotic tissues, and cut into several small fragments approximately 2 mm in length for transplantation. Four-eight week old wild-type recipient mice syngeneic to the FVB/N background were anesthetized by isoflourane inhalation (2-4%). The abdominal area was shaved and cleaned with betadine disinfectant and a 0.5-cm incision was made on the distal side of the 4th mammary gland just above the subcutaneous fat tissue. The subcutaneous mammary fat was then gently exposed using sterile blunted-end forceps to create a pocket where tumor fragments were immediately seeded. The incision was closed with wound clips and tumor growth was monitored weekly. Twelve different transplantable tumor graft lines from twelve distinct tumors were established. Each transplantation line was sequentially passaged and re-sampled from multiple regions at different passage generations to build a repository of transgenic grafts for molecular analysis. These transplants could be readily frozen in 95% FBS and 10% dimethyl sulfoxide (DMSO), stored in liquid nitrogen, and reactivated again as needed.

For treatment, talazoparib was dissolved in a solution composed of 0.5% hydroxypropylmethylcellulose (Sigma), 0.2% Tween 80, and 2% DMSO in distilled water (pH 8.0) and administered daily via oral gavage at a concentration 0.01 mg/mouse. Treatment was initiated after transplants reached palpable size.

Figure 11:
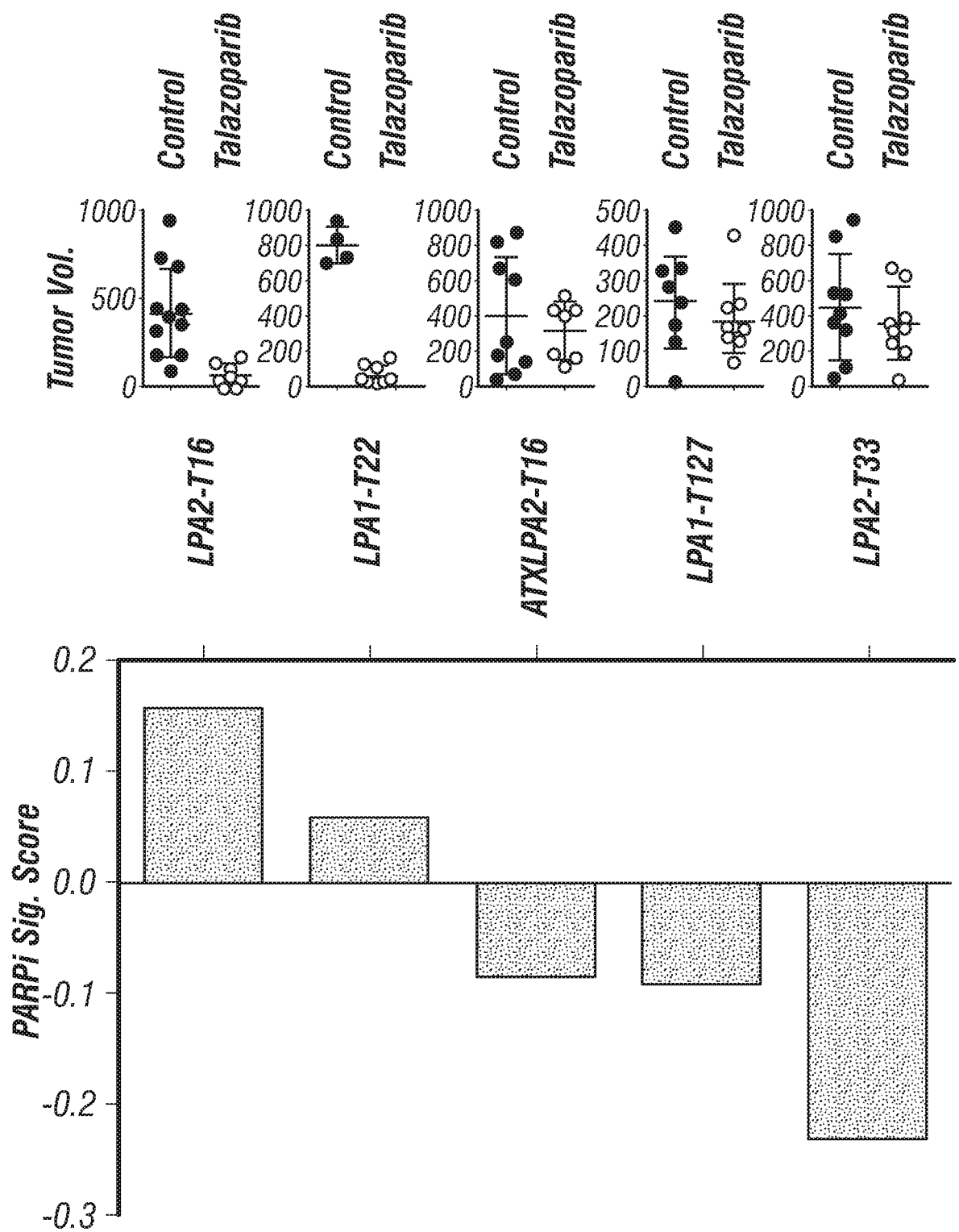
FIG. 11: Tumor volume of mice treated with control or Talazoparib and the corresponding PARP inhibitor signature scores are shown.

RNA-seq paired-end reads of eighteen samples collected from nine MDST models (2 samples per model) and two normal murine mammary gland samples were mapped to the mouse reference genome (NCBIM37) using Tophat2 (v2.0.10). The mouse annotation file (ENSEMBL NCBIM37 release 66) was used to guide spliced alignment of known transcripts. Only uniquely mapped reads were kept for further analysis. A standard Counts Per Million (CPM), representing mapped reads counts normalized by the number of sequenced fragments multiplied by one million, was calculated for each gene and used to calculate PARPi sensitivity score as shown in FIG. 11. The PARP inhibitor signature score was able to predict response to talazoparib in all of the mice.

Collectively, by summarizing large-scale genomic data, this work has allowed for complex datasets to be placed in a biological context that may be used to provide molecularly tailored treatment recommendations, and also provide a foundation for the discovery of synergistic therapies that could be further tested or used for individualized care. The predictive algorithm that we have generated, may not only prove useful in the clinical setting for guiding treatment decisions, but may also be generalized to answer additional questions from other human diseases that require similar interrogation.

Example 2—Materials and Methods

Iterative resampling analysis to predict sensitivity (IRAPS): Gene expression data for 857 solid-tumor derived cancer cell lines was downloaded from the CCLE database. Data were log 2 transformed, quantile-normalized, and median polished on a per-tissue type basis. This data was then combined with drug sensitivity data from either the Genomics of Drug Sensitivity in Cancer (GDSC) dataset (PARP inhibitors, cisplatin) (O'Neil et al., 2012), or from the Cancer Therapeutic Response Portal v2 (HER2 inhibitors) (Seashore-Ludlow et al., 2015).

To determine a list of differentially expressed genes, a random selection of 50% of available cell lines were sampled and sensitivity values (the half maximal inhibitor concentration ($IC_{50}$) for GDSC and area under the curve (AUC) for the drug dose response curve for CTRPv2) converted into z-scores, which were used to define a class of "responders" (z-score<−1) and "non-responders" (z-score>0). To improve predicative capacity, the average z-score of two inhibitors was used to define sensitivity for PARP (rucaparib and olaparib) and HER2 inhibitors (lapatanib and neratanib) enforcing that responders both had a minimal z-score of −0.5 and both non-responders had z-scores greater than zero.

This resulted in approximately 20% of cells being classified as responders, 50% as non-responders, and 30% falling into neither category. Specifically, approximately 30 responders/110 non-responders were identified for HER2 inhibitors per iteration, 25 responders/70 non-responders for cisplatin, and 15 responders/50 non-responders PARP inhibitors. For each panel a sub set of samples was excluded for testing the signatures: for testing the HER2 signature 2 samples were excluded for HER2 inhibitors plus 16 additional that were tested for afatinib but not lapatanib and neratanib, for testing the cisplatin signature half of basal breast cancer cell lines were excluded, and for testing the PARP inhibitor signature all cell lines screened against BMN-673 were excluded from training. This process was repeated 1000 times by selecting a different random population each time to generate 1000 lists of differentially expressed genes. To refine these gene expression datasets that were generated across all solid tumors, a grid-search optimization algorithm was used to maximize the accuracy of prediction in the desired tumor types across all combinations of gene fold changes, p-values, and conservation across the multiple iterations—that is the frequency a gene was found to be altered at a given p-value and fold change threshold. At each threshold, the average gene fold change for each gene meeting the specified criteria was used as the gene weight. For example, for p=1e-4, fold change=1.25, and conservation value of 0.8 the signature would consist of all genes that had p-values <1e-4 and fold changes >1.25 in at least 800/1000 iterations, with weights consisting of the average fold changes across all runs for these genes. Signature scores were determined by calculating the correlation coefficient between gene weights within the signature and gene expression levels for that gene within a given sample. For the HER2 inhibitor signature this was breast cancer, for cisplatin a combination of endometrial and basal breast cancer was used to preserve the ovarian cancer lines for testing, and for the PARP inhibitors ovarian and breast cancers were used. The derived signatures were tested against afatinib treated breast cancer for the HER2 signature, ovarian cancer and the remaining half of basal breast cancer cell lines for cisplatin, and BMN-673 treated breast and ovarian cancer cell lines for the PARPi signature. All sensitivity signatures are included in Tables 1, 2, and 4.

Patient survival analysis: The cisplatin sensitivity signature was used to predict patient prognosis for ovarian cancer patients that were treated with cisplatin in two independent cohorts, Hennessy (Peng et al., 2014) and Bowtell (Tothill et al., 2008). Signature scores were calculated following quantile normalization. To generate Kaplan-Meier curves, patients were divided based on the maximization of statistical difference in signature scores between the two groups. To account for stage and grade as covariates, a Cox proportional hazards model was used.

Cell line screening of BMN-673 sensitivity: Drugs were 3-fold serial diluted for 7 dilutions in DMSO at 1,000× concentration stocks. Aliquots of the diluted stocks were stored in deep-well "master plates" in −20° C. Cancer cell lines involved in this assay were verified by short tandem repeat (STR) analysis (CCSG Characterized Cell Line Core in MD Anderson Cancer Center). Cell lines were maintained in their optimal growth medium (with 5% FBS) and seeded in 96-well plates at 2,500 cells/100 μL/well for 24-hour incubation prior to be changed into the medium containing 2% FBS for overnight incubation. Serial diluted drug stocks were added to each well to make 1/1,000 final concentration for additional 7-day incubation. DMSO at 0.1% without any drugs was used as controls. Triplicates were performed for testing each concentration. Cell viability was determined by using the Cell Titer Blue Cell Viability Assay (5 μL of the reagent/well) and measured at 530Ex/604Em. Cell viability was defined by $GI_{50}$ concentration, defined as the concentration required to slow cell growth by 50%, calculated according to a cell viability curve.

Patient-derived tumor cells: The sensitivity of patient-derived tumor cells to BMN-673, along with relevant gene expression and mutation data, was acquired from the work of Bruna and colleagues (Bruna et al., 2016). Data for the PDX models HCI-001, HCI-006, and HCI-010 were excluded from analysis as they were used for in vivo testing. For models that had multiple replicates, the earliest passage explant matched with the nearest passage of gene expression data was analyzed.

Patient-derived xenografts: Patient-derived breast cancer xenografts (HCI-001, HCI-006, HCI-010) with matching RNAseq data (GSE32532) were acquired from the University of Utah Patient-Derived Xenograft Repository and implanted as described into athymic nu/nu mice (DeRose et al., 2011). After reaching a volume of 100 mm³ treatment was initiated via intraperitoneal injection with 50 mg/kg AZD2281 or with 40% PEG400 as the vehicle control. Treatments were given QD for 28 consecutive days as previously described (Rottenberg et al., 2008). The study made use of ten mice per treatment arm, and tumor volumes were tracked with calipers in order to calculate tumor volumes as (length×width2)/2. End-point mice were sacrificed by carbon dioxide inhalation. The treatment of animals were done in accordance with Institutional Animal Care and Use Committee (IACUC) protocols at MD Anderson Cancer Center. Tumor volumes were reported as their mean±SEM.

PARP inhibitor synergizing agents: In order to predict drugs that may sensitize cells using the PARP sensitivity signature, the lincscloud database was used that compares the current signature with thousands of chemical perturbations. A ranked list of candidate molecules was obtained, and then verified the top hits in breast cancer and ovarian cell lines that were available. Based on this analysis, PKCβ inhibition was identified as a top hit, and the PKCβ Enzastaurin (LY317615) was tested in combination with the PARP inhibitor BMN-673 using a molar ratio of 3:1, respectively. Cells were treated for 5 days with either LY317615, BMN-673, or in combination before we analyzed cell viability with PrestoBlue (Invitrogen) per the manufacturer's instructions. Each independent replicate was performed with 2 technical replicates. Combination indices (CI) were calculated using CompuSyn software (Chou, 2006), where values under 1 represented synergism and values over 1 represented antagonism.

Homologous recombination assays: Homologous recombination activity was assessed by two separate approaches. First, the DR-GFP reporter assay was utilized as previously described (Peng, 2014). Briefly, cells were transfected with equimolar amounts of either a combination of direct repeat GFP (DR-GFP) and pCBASceI (gifts from Dr. Maria Jasin; Memorial Sloan-Kettering Cancer Center, New York, N.Y.) using Lipofectamine 3000 (Invitrogen), which induces green fluorescence in cells with an active homologous recombination machinery, or by using a GFP-expressing plasmid (pEGFP-C1) as a transfection efficiency control. The day following transfection, cells were treated with 5 μM LY317615 and then harvested 48 hours later for flow cytometry analysis. GFP positive cells were gated based on SSC-FITC scatter plots. Percentages of cells with active homologous recombination were calculated as 100× (% DR-GFP$^+$ cells)/(% pEGFP$^+$ cells), with at least 50,000 cells having been analyzed per condition. Additionally the ability of cells to form RAD51 foci following gamma irradiation was analyzed. Cells were pre-treated with 5 μM LY317615 for 4 hours before treatment with 5 Gy radiation. After recovering for 4 hours, cells were stained for RAD51 foci as previously described (Peng et al., 2009) with an anti-RAD51 antibody (sc8349, Santa Cruz Biotechnology). Cells were imaged and analyzed by fluorescence microscopy (Eclipse TE2000E, Nikon) and automatically quantified in a custom-written MATLAB algorithm (MathWorks). Cells with more than 10 foci were counted as positive, with a minimum of 50 cells scored across 3 independent experiments for at least 150 cells in total per condition.

Prediction of drugs targeting the BRCAness signature: Prediction of BRCAness-targeting drugs was carried out using drug sensitivity data from the CTRPv2 database. For this analysis, expression data of ovarian cancer cell lines (excluding those that were used for testing) was extracted and quantile normalized before calculating a BRCAness score based on a previously established BRCAness signature (Konstantinopoulos et al., 2010). Cells with BRCAness scores that were greater than 1 standard deviation above the average were considered positive, and cells with a below average score were considered negative. The drug sensitivity data for these cell lines were extracted and used to identify drugs that specifically targeted cells with high levels of BRCAness. Drugs were selected that were both selective and had high toxicities in the BRCA-like group, which were defined as area under response curve values of 9 or less, and tested in COV362 (BRCA1 mutant), A2780 (BRCA-like), ES2 (non-BRCA-like), and OVCAR8 (non-BRCA-like) cells. Additionally, molecules that BRCA-like cells were predicted to be resistant to were also tested. For these studies, cells were plated at 5,000 cells/well in a 96 well plate and treated with serial dilutions of specified drugs for 72 hours before viability quantification with PrestoBlue.

Statistical analysis: Unless otherwise noted, statistical significance was determined by either using a student t-test or a two-way ANOVA with post-hoc analysis from triplicate independent experiments. All data are reported as the mean±standard error of the mean (SEM).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel et al., John Wiley & amp; Sons, New York, N.Y. (2003).
Barretina, J. et al. Nature 483, 603-7 (2012).
Bast, R. C. & Mills, G. B. P. J. Clin. Oncol. 28, 22-25 (2014).
Brown, J. S., et al. Br. J. Cancer 114, 713-715 (2016).
Bruna, A. et al. Cell 167 (2016).
Bryant, H. E. et al. Nature 434, 913-7 (2005).
Cardoso, F. et al. N. Engl. J. Med. 375, 717-729 (2016).
Chou, T.-C. Pharmacol. Rev. 58, 621-681 (2006).
Costello, J. C. et al. Nat. Biotechnol. 32, 1-103 (2014).
Cowin, P. et al. Annu. Rev. Genomics Hum. Genet. 11, 133-59 (2010).
DeRose, Y. S. et al. Nat. Med. 17, 1514-20 (2011).
Garnett, M. J. et al. Nature 483, 570-5 (2012).
Kang, J., D'Andrea, A. D. & Kozono, D. J. Natl. Cancer Inst. 104, 670-681 (2012).
Koboldt, D. C. et al. Nature 490, 61-70 (2012).
Konecny, G. E. et al. Cancer Res. 66, 1630-9 (2006).
Konstantinopoulos, P. A. et al. J. Clin. Oncol. 28, 3555-3561 (2010).
Li, W. & Melton, D. W. Oncogene 31, 2412-2422 (2012).
Livraghi, L. & Garber, J. E. BMC Med. 13, 188 (2015).
Lord, C. J. & Ashworth, A. Nat. Rev. Cancer 16, 110-120 (2016).
O'Neill, F. et al. Mol. Cancer 11, 41 (2012).
Olaussen, K. A. et al. N. Engl. J. Med. 355, 983-991 (2006).
Paez, J. G. et al. Science 304, 1497-500 (2004).
Peng, G. et al. Nat. Cell Biol. 11, 865-872 (2009).
Peng, G. et al. Nat. Commun. 5, 3361 (2014).
Pitroda, S. P. et al. Sci. Transl. Med. 6, 229ra42 (2014).
Rottenberg, S. et al. Proc. Natl. Acad. Sci. 105, 17079-17084 (2008).
Sambrook et al., Cold Spring Harbor Press, Cold Spring Harbor, N.Y. (1989).
Scappini, B. et al. Cancer 100, 1459-71 (2004).
Seashore-Ludlow, B. et al. Cancer Discov. 5, 1210-1223 (2015).
Tothill, R. W. et al. Clin. Cancer Res. 14, 5198-5208 (2008).
Wallden, B. et al. BMC Med. Genomics 8, 54 (2015).
Yang, W. et al. Nucleic Acids Res. 41, 955-961 (2013).
International Patent Publication No. WO 2006/110816
International Patent Publication No. WO 2008/083027
International Patent Publication No. WO 2009/024824
International Patent Publication No. WO 2011/014681
International Patent Publication No. WO 2011/063907
International Patent Publication No. WO 2011/063908
International Patent Publication No. WO 2011/064328
International Patent Publication No. WO 2012/082997
International Patent Publication No. WO 2014/005182
International Patent Publication No. WO2010/006072
International Patent Publication No. WO2010/007756
International Patent Publication No. WO2010/027827
International Patent Publication No. WO2011/066342
International Patent Publication No. WO2013131962
International Patent Publication No. WO2015016718
U.S. Pat. No. 5,538,848
U.S. Pat. No. 5,716,784
U.S. Pat. No. 5,723,591
U.S. Pat. No. 7,473,767
U.S. Pat. No. 7,928,105
U.S. Pat. No. 8,008,449
U.S. Pat. No. 8,019,552
U.S. Pat. No. 8,124,606
U.S. Pat. No. 8,236,802
U.S. Pat. No. 8,354,509
U.S. Pat. No. 8,450,323
U.S. Pat. No. 8,535,889
U.S. Pat. No. 8,586,574
U.S. Pat. No. 8,735,553
U.S. Patent Publication No. US2003/0045491
U.S. Patent Publication No. US2007/0112005
U.S. Patent Publication No. US2007/0149521
U.S. Patent Publication No. US2007/0254883
U.S. Patent Publication No. US2009/0312319
U.S. Patent Publication No. US2010/0015140
U.S. Patent Publication No. US2010/0048547
U.S. Patent Publication No. US2011/0002923
U.S. Patent Publication No. US20110008369
U.S. Patent Publication No. US20130259858
U.S. Patent Publication No. US2014022021
U.S. Patent Publication No. US20140294898
U.S. Patent Publication No. US20140357660

The invention claimed is:

1. A method of treating a cancer in a subject comprising:
(a) determining the expression levels of at least genes ZNF880, CAPN13, LYAR, and NPM3 from the group consisting of SNX10, ECI2, DBN1, TNFRSF10B, NPM3, CATSPER1, PRMT3, FAM216A, LYAR, NOP16, THG1L, LOC439949, TMA16, GEMIN4, HAUS6, SFXN4, SAAL1, NUP160, ESD, TSEN15, KIAA1704, HSPA4, SFXN1, NAT10, C11orf48, TSEN2, HEATR2, GEMIN5, IMPDH2, NOC3L, ERLIN1, C1QBP, EIF3M, MTHFD1L, MTX3, MRPS27, PPRC1, TCOF1, IDE, RNF2, WDR75, NAA15, DDX21, RARS, ALG8, BOLA3, EARS2, FAF2, MRPL42, ATIC, NUP37, RPL36, GNB2L1, NPBWR1, GALNTL5, LOC729173, LOC441461, KALRN, ADCY2, MTHFR, MS4A7, RNF186, IRF4, WBSCR17, CLEC7A, WDTC1, PRKG2, OSTalpha, DUSP18, LOC100652843, FAIM2, TNNI2, SEZ6, LOC285556, KCNQ1, KLF8, VPS13D, NR0B2, TMEM86A, DCAF5, SOS2, CAPN9, RIPK3, TPRXL, CELF4, ATP6V1E1, ZBTB7C, CATSPERB, CAPN13, MMEL1, ELF5, C2orf54, DVL3, SIRT2, LOC641518, IL12RB2, CBFA2T2, LINC00518, OSBPL2, SH3GLB1, CHMP4B, HSD11B2, ACVR1C, TMEM61, DLL3, CXCL17, SLC44A4, RNF183, KLK8, RIIAD1, ATP7A, GJB1, BCAS1, SCGN, TTC3, IGSF11, LOC440335, LOC645591, C4orf3, LRRC31, ADAM12, BHLHE41, RNASE1, PPP1R3B, LOC100505989, CAPN8, C2CD4A, CHGA, ERBB2, NELL1, FAM174B, CALML5, TSC22D3, C9orf152, KLK6, MB, ST6GALNAC1, SFTA2, MUC1, SETBP1, SCG3, PRUNE2, SSPN, CEACAM5, TMEM45B, MAFB, and ZNF880 in a sample comprising cancer cells from said subject;

(b) identifying the subject as having a PARP inhibitor sensitive cancer by calculating a signature score from the expression levels of the genes, wherein a positive signature score identifies the subject as having a PARP inhibitor sensitive cancer; and (c) administering an effective amount of a PARP inhibitor to said subject identified to have a PARP inhibitor sensitive cancer.

2. The method of claim 1, wherein the cancer cells are breast cancer cells or ovarian cancer cells.

3. The method of claim 1, wherein the sample is blood, saliva, urine, or a tissue biopsy.

4. The method of claim 1, further comprising determining the expression levels of at least 5, 6, 7, 8, 9 or 10 genes.

5. The method of claim 1, wherein determining the expression levels comprises performing RT-PCR, hybridization, transcriptome analysis, a Northern blot, a Western blot, RNA sequencing, or an ELISA.

6. The method of claim 1, further comprising administering to the subject at least a second anti-cancer therapy.

7. The method of claim 6, wherein the at least a second anti-cancer therapy is chemotherapy, immunotherapy, surgery, radiotherapy, or biotherapy.

8. The method of claim 6, wherein the subject is treated with a PARP inhibitor and the PARP inhibitor and the at least a second anti-cancer therapy are administered simultaneously.

9. The method of claim 6, wherein the PARP inhibitor is administered to the subject prior to the at least a second anti-cancer therapy.

10. The method of claim 6, wherein the at least a second anti-cancer therapy is a PKCβ inhibitor.

11. The method of claim 10, wherein the PKCβ inhibitor is Enzastaurin.

12. The method of claim 1, wherein the PARP inhibitor is talazoparib, olaparib, ABT-888, Iniparib, BMN 673, Rucaparib, AG14361, INO-1001, A-966492, PJ34, or MK-4827.

13. The method of claim 1, wherein determining the expression levels comprises determining expression levels relative to a healthy control, and determining relative fold changes, and step (b) further comprises determining gene expression z-scores from relative gene fold changes.

14. The method of claim 13, wherein determining the signature score comprises summing the product of each gene expression z-score multiplied by its corresponding refined coefficient, wherein genes SNX10, ECI2, DBN1, TNFRSF10B, NPM3, CATSPER1, PRMT3, FAM216A, LYAR, NOP16, THG1L, LOC439949, TMA16, GEMIN4, HAUS6, SFXN4, SAAL1, NUP160, ESD, TSEN15, KIAA1704, HSPA4, SFXN1, NAT10, C11orf48, TSEN2, HEATR2, GEMIN5, IMPDH2, NOC3L, ERLIN1, C1QBP, EIF3M, MTHFD1L, MTX3, MRPS27, PPRC1, TCOF1, IDE, RNF2, WDR75, NAA15, DDX21, RARS, ALG8, BOLA3, EARS2, FAF2, MRPL42, ATIC, NUP37, RPL36, and GNB2L1 have a refined coefficient of positive 1, and genes NPBWR1, GALNTL5, LOC729173, LOC441461, KALRN, ADCY2, MTHFR, MS4A7, RNF186, IRF4, WBSCR17, CLEC7A, WDTC1, PRKG2, OSTalpha, DUSP18, LOC100652843, FAIM2, TNNI2, SEZ6, LOC285556, KCNQ1, KLF8, VPS13D, NR0B2, TMEM86A, DCAF5, SOS2, CAPN9, RIPK3, TPRXL, CELF4, ATP6V1E1, ZBTB7C, CATSPERB, CAPN13, MMEL1, ELF5, C2orf54, DVL3, SIRT2, LOC641518, IL12RB2, CBFA2T2, LINC00518, OSBPL2, SH3GLB1, CHMP4B, HSD11B2, ACVR1C, TMEM61, DLL3, CXCL17, SLC44A4, RNF183, KLK8, RIIAD1, ATP7A, GJB1, BCAS1, SCGN, TTC3, IGSF11, LOC440335, LOC645591, C4orf3, LRRC31, ADAM12, BHLHE41, RNASE1, PPP1R3B, LOC100505989, CAPN8, C2CD4A, CHGA, ERBB2, NELL1, FAM174B, CALML5, TSC22D3, C9orf152, KLK6, MB, ST6GALNAC1, SFTA2, MUC1, SETBP1, SCG3, PRUNE2, SSPN, CEACAM5, TMEM45B, MAFB, and ZNF880 have a refined coefficient of −1.

15. The method of claim 1, wherein step (a) comprises determining the expression levels of at least 40 genes.

16. The method of claim 15, wherein the at least 40 genes are ALG8, C1QBP, CAPN13, CATSPERB, CEACAM5, CHMP4B, DVL3, ERBB2, ESD, GEMIN4, GJB1, HEATR2, HSD11B2, IDE, KCNQ1, LRRC31, LYAR, MB, MMEL1, MRPS27, MTHFR, NAT10, NPM3, NUP37, OSTalpha, PPRC1, PRKG2, PRMT3, RARS, RNF183, RNF2, SCGN, SEZ6, SFTA2, SOS2, TCOF1, TMEM61, TSEN15, WDTC1, and ZNF880.

17. The method of claim 1, wherein step (a) comprises determining the expression levels of at least 30 genes.

18. The method of claim 17, wherein the at least 30 genes are NPM3, LYAR, GEMIN4, TSEN15, KIAA1704, NAT10, HEATR2, C1QBP, RARS, ALG8, NUP37, ATP7A, DDX21, MTHFR, WDTC1, PRKG2, OSTalpha, SEZ6, KCNQ1, CATSPERB, CAPN13, DVL3, HSD11B2, RNF183, SCGN, ERBB2, LRRC31, MB, SFTA2, and ZNF880.

19. The method of claim 1, wherein step (a) comprises determining the expression levels of at least 20 genes.

20. The method of claim 19, wherein the at least 20 genes selected from the group consisting of ALG8, CAPN13, ESD, TSEN15, GEMIN4, GJB1, HEATR2, IDE, KCNQ1, LYAR, NPM3, OSTalpha, PPRC1, RARS, RNF183, SCGN, SEZ6, SFTA2, WDTC1, and ZNF880.

21. The method of claim 1, wherein step (a) comprises determining the expression levels of at least 10 genes.

22. The method of claim 21, wherein the at least 10 genes are ALG8, CAPN13, ESD, HEATR2, IDE, LYAR, MB, NPM3, THG1L, and ZNF880.

23. The method of claim 1, further comprising measuring the expression of IDE.

24. The method of claim 1, further comprising measuring the expression of IDE and GJB1.

25. The method of claim 1, further comprising measuring the expression of IDE, GJB1 and PPRC1.

26. The method of claim 1, further comprising measuring the expression of IDE, GJB1, PPRC1 and GEMIN4.

27. The method of claim 1, further comprising measuring the expression of IDEGJB1, WDTC1, SCGN, and PPRC1.

28. The method of claim 1, further comprising measuring the expression of PPRC1, GJB1 OSTalpha and RARS.

29. The method of claim 1, further comprising measuring the expression of IDESFTA1, SCGN, GHB1, and EST.

30. The method of claim 1, wherein the expression levels are quantile-normalized and median polished.

* * * * *